United States Patent
Seganish et al.

(10) Patent No.: US 9,586,948 B2
(45) Date of Patent: Mar. 7, 2017

(54) INHIBITORS OF IRAK4 ACTIVITY

(71) Applicant: MERCK SHARP & DOHME CORP., Rahway, NJ (US)

(72) Inventors: W. Michael Seganish, Scotch Plains, NJ (US); Jennifer Hanisak, Stewartsville, NJ (US); Guoqing Li, Belle Mead, NJ (US); Rui Zhang, Plainsboro, NJ (US); Haiqun Tang, Belle Mead, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/434,348

(22) PCT Filed: Oct. 3, 2013

(86) PCT No.: PCT/US2013/063173
§ 371 (c)(1),
(2) Date: Apr. 8, 2015

(87) PCT Pub. No.: WO2014/058691
PCT Pub. Date: Apr. 17, 2014

(65) Prior Publication Data
US 2015/0274708 A1    Oct. 1, 2015

Related U.S. Application Data

(60) Provisional application No. 61/710,958, filed on Oct. 8, 2012.

(51) Int. Cl.
| | |
|---|---|
| C07D 401/04 | (2006.01) |
| C07D 409/14 | (2006.01) |
| C07D 401/14 | (2006.01) |
| C07D 405/14 | (2006.01) |
| C07D 401/12 | (2006.01) |
| C07D 417/14 | (2006.01) |
| A61K 45/06 | (2006.01) |
| A61K 31/4439 | (2006.01) |
| A61K 31/444 | (2006.01) |
| A61K 31/496 | (2006.01) |
| A61K 31/506 | (2006.01) |
| A61K 31/5377 | (2006.01) |
| A61K 31/497 | (2006.01) |

(52) U.S. Cl.
CPC ......... *C07D 409/14* (2013.01); *A61K 31/444* (2013.01); *A61K 31/4439* (2013.01); *A61K 31/496* (2013.01); *A61K 31/497* (2013.01); *A61K 31/506* (2013.01); *A61K 31/5377* (2013.01); *A61K 45/06* (2013.01); *C07D 401/12* (2013.01); *C07D 401/14* (2013.01); *C07D 405/14* (2013.01); *C07D 417/14* (2013.01)

(58) Field of Classification Search
CPC .................................................... C07D 401/04
USPC ........................................ 546/275.4; 514/341
See application file for complete search history.

(56) References Cited

U.S. PATENT DOCUMENTS

| | | | |
|---|---|---|---|
| 8,148,411 | B2 | 4/2012 | Bothe et al. |
| 2011/0152260 | A1 | 6/2011 | Guckian et al. |
| 2011/0306589 | A1 | 12/2011 | Bleicher et al. |
| 2012/0115861 | A1 | 5/2012 | Calderini et al. |

FOREIGN PATENT DOCUMENTS

| | | |
|---|---|---|
| WO | WO2011006567 | 1/2011 |
| WO | WO2011043371 | 4/2011 |
| WO | WO2012129258 | 9/2012 |
| WO | WO2013042137 | 3/2013 |

OTHER PUBLICATIONS

Dorwald, Side Reactions in Organic Synthesis, 2005, Wiley: VCH Weinheim Preface, pp. 1-15 & Chapter 8, pp. 279-308.*
Buckley, George M. et al, IRAK-4 INHIBITORS. Part 1: A Series of Amides, Bioorganic & Medicinal Chemistry Letters, 2008, 3211-3214, 18.
Buckley, George M. et al, IRAK4 Inhibitors. Part II: A Structure-Based Assessment of Imidazo [1,2-a]Pyridine Binding, Bioorganic & Medicinal Chemistry Letters, 2008, 3291-3295, 18.
Buckley, George M. et al, IRAK4 Inhibitors. Part III: A Series of Imidazo[1,2-a] Pyridines, Bioorganic & Medicinal Chemistry Letters, 2008, 3656-3660, 18.
Powers, Jay et al, Discovery and Initial SAR of Inhibitors of Interleukin-1 Receptor-Associated Kinase-4, Bioorganic & Medicinal Chemistry, 2006, 2842-2845, 16.
Wang, Zhulun et al, IRAK-4 Inhibitors for Inflammation, Current Topics in Medicinal Chemistry, 2009, 724-737, vol. 9, San Francisco.

* cited by examiner

*Primary Examiner* — Patricia L Morris
(74) *Attorney, Agent, or Firm* — Matthew A. Leff; John C. Todaro

(57) ABSTRACT

The present invention relates to inhibitors of IRAK4 of Formula (I) and provides compositions comprising such inhibitors, as well as methods therewith for treating IRAK4-mediated or -associated conditions or diseases.

3 Claims, No Drawings

INHIBITORS OF IRAK4 ACTIVITY

BACKGROUND OF THE INVENTION

The present invention is directed to compounds which modulate interleukin-1 (IL-1) receptor-associated kinase 4 (IRAK4) and are useful in the prevention or treatment of inflammatory, cell proliferative and immune-related conditions and diseases.

The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration observed in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, sepsis, etc.

The importance of IL-1 in inflammation has been demonstrated by the ability of the highly specific IL-1 receptor antagonist protein (IL-1Ra or IRAP) to relieve inflammatory conditions. See, e.g., Dinarello, Cytokine Growth Factor Rev., 1997, 8:253-265.

IL-1 treatment of cells induces the formation of a complex consisting of the two IL-1 receptor chains, IL-1R1 and IL-1RAcP, and the resulting heterodimer recruits an adaptor molecule designated as MyD88. See e.g., Wesche et al., J. Biol. Chem., 1999, 274:19403-19410. MyD88 binds to a protein designated IRAK (IL-1 receptor associated kinase). See, e.g., O'Neill et al., J. Leukoc. Biol., 1998, 63(6):650-657; Auron, Cytokine Growth Factor Rev., 1998, 9(3-4):221-237; and O'Neill, Biochem. Soc. Trans., 2000, 28(5):557-563. IRAK is subsequently phosphorylated and released from the receptor complex to interact with a tumor necrosis factor receptor-associated factor, TRAF6, which transduces the signal to downstream effector molecules. See e.g., Cao et al., Nature, 1996, 383:443-446. TRAF6 can trigger the NIK/IKK kinase cascade to activate the transcription factor NK-kappa B. NF-kappa B regulates a number of genes that, in turn, regulate immune and inflammatory responses.

Four IRAKs have been identified: IRAK1 (see, e.g., Cao et al., Science, 1996, 271:1128-1131), IRAK2 (see, e.g. Muzio et al., Science, 1997, 278:1612-1615), the monomyeloic cell specific IRAKM, also known as IRAK3 (see, e.g., Wesche et al., J. Biol. Chem., 1999, 274:19403-19410), and IRAK4 (see, e.g., PCT Publication No. WO 01/051641). IRAK proteins have been shown to play a role in transducing signals other than those originating from IL-1 receptors, including signals triggered by activation of IL-18 receptors (see, e.g., Kanakaraj et al., J. Exp. Med., 1999, 189(7):1129-1138) and LPS receptors (see, e.g., Yang et al., J. Immunol., 1999, 163:639-643; and Wesche et al., J. Biol. Chem., 1999, 274:19403-19410). Over-expression of IRAK2 and IRAKM has been shown to be capable of reconstituting the response to IL-1 and LPS in an IRAK deficient cell line.

The identification of compounds that inhibit the function of IRAK4 represents an attractive approach to the development of therapeutic agents for the treatment of inflammatory, cell proliferative and immune-related conditions and diseases associated with IRAK4-mediated signal transduction, such as rheumatoid arthritis, inflammatory bowel disease, multiple sclerosis, diabetes, obesity, allergic disease, psoriasis, asthma, graft rejection, cancer, and sepsis.

It is an object of the instant invention to provide novel compounds that are inhibitors of IRAK4.

It is also an object of the present invention to provide pharmaceutical compositions that comprise the novel compounds that are inhibitors of IRAK4.

It is also an object of the present invention to provide a method for treating IRAK4-mediated and associated conditions or diseases that comprises administering such inhibitors of IRAK4 activity.

SUMMARY OF THE INVENTION

The present invention relates to inhibitors of IRAK4 of formula (1) and provides compositions comprising such inhibitors, as well as methods therewith for treating IRAK4-mediated or associated conditions or diseases.

DETAILED DESCRIPTION OF THE INVENTION

The compounds of the instant invention are useful in the inhibition of the activity of IRAK4.

An embodiment of the instant invention is illustrated by the Formula I:

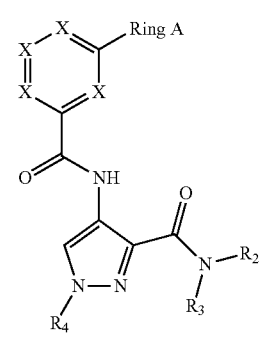

wherein:
X is CH or N;
a is 0 or 1; b is 0 or 1; m is 0, 1 or 2;
Ring A is $(C_3-C_8)$cycloalkyl, $(C_3-C_8)$cycloalkenyl, aryl or heterocycle optionally substituted with one to three substituents independently selected from $R_1$;
$R_1$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$fluoroalkyl, $(C=O)_aNR_5R_6$, CN, $(C=O)_aO_b(C_3-C_8)$cycloalkyl, $S(O)_mNR_5R_6$, SH, $S(O)_m-(C_1-C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;
$R_2$ and $R_3$ are independently selected from: H, $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, CN, $O_bC_1-C_6$ fluoroalkyl, $O_a(C=O)_bNR_5R_6$, CHO, $(N=O)R_5R_6$, $S(O)_mNR_5R_6$, SH, $S(O)_m-(C_1-C_{10})$alkyl, $(C=O)_aO_bC_3-C_8$ cycloalkyl, optionally substituted with one or more substituents selected from $R_1$; or $R_2$ and $R_3$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R_1$;

$R_4$ is selected from: $(C_1-C_6)$alkyl and $(C_3-C_6)$cycloalkyl, optionally substituted with $R_a$;

$R_5$ and $R_6$ are independently selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, $O_b(C_1-C_6)$fluoroalkyl, $(C=O)_aN(R_a)_2$, CN, $(C=O)_aO_b(C_3-C_8)$cycloalkyl, $S(O)_m$ $N(R_a)_2$, SH, $S(O)_m$—$(C_1-C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;

$R_a$ is independently selected from $R_b$, OH, $(C_1-C_6)$alkoxy, halogen, cyclopropyl, $CO_2H$, CN, $O_a(C=O)_b(C_1-C_6)$alkyl, oxo, and $N(R_b)_2$; and $R_b$ is independently selected from H and $(C_1-C_6)$alkyl;

or a pharmaceutically acceptable salt or a stereoisomer thereof.

Another embodiment of the instant invention is illustrated by the Formula II:

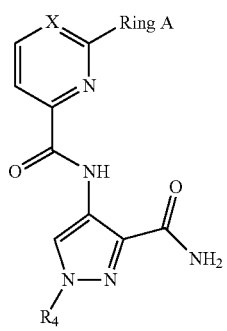

wherein:
X is CH or N;
a is 0 or 1; b is 0 or 1; m is 0, 1 or 2;
Ring A is selected from phenyl and heterocyclyl optionally substituted with one to three substituents independently selected from $R_1$;

$R_1$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR_5R_6$, CN, $(C=O)_aO_b(C_3-C_8)$cycloalkyl, $S(O)_mNR_5R_6$, SH, $S(O)_m$—$(C_1-C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;

$R_4$ is selected from: $(C_1-C_4)$alkyl optionally substituted with OH, methoxy and halogen;

$R_5$ and $R_6$ are independently selected from: H, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, $O_b(C_1-C_6)$fluoroalkyl, $(C=O)_aN(R_a)_2$, CN, $(C=O)_aO_b(C_3-C_8)$cycloalkyl, $S(O)_m$ $N(R_a)_2$, SH, $S(O)_m$—$(C_1-C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;

$R_a$ is independently selected from $R_b$, OH, $(C_1-C_6)$alkoxy, halogen, cyclopropyl, $CO_2H$, CN, $O_a(C=O)_b(C_1-C_6)$alkyl, oxo, and $N(R_b)_2$; and $R_b$ is independently selected from H and $(C_1-C_6)$alkyl;

or a pharmaceutically acceptable salt or a stereoisomer thereof.

Another embodiment of the instant invention is illustrated by the Formula III:

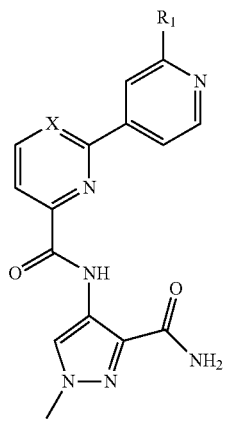

wherein:
X is CH or N;
a is 0 or 1; b is 0 or 1; m is 0, 1 or 2;
$R_1$ is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR_5R_6$, CN, $(C=O)_aO_b(C_3-C_8)$cycloalkyl, $S(O)_mNR_5R_6$, SH, $S(O)_m$—$(C_1-C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;

$R_5$ and $R_6$ are independently selected from: H, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, $O_b(C_1-C_6)$perfluoroalkyl, $(C=O)_aN(R_a)_2$, CN, $(C=O)_aO_b(C_3-C_8)$cycloalkyl, $S(O)_m$ $N(R_a)_2$, SH, $S(O)_m$—$(C_1-C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;

$R_a$ is independently selected from $R_b$, OH, $(C_1-C_6)$alkoxy, halogen, cyclopropyl, $CO_2H$, CN, $O_a(C=O)_b(C_1-C_6)$alkyl, oxo, and $N(R_b)_2$; and $R_b$ is independently selected from H and $(C_1-C_6)$alkyl;

or a pharmaceutically acceptable salt or a stereoisomer thereof.

A compound of the instant invention is selected from:
N-(3-carbamoyl-1-methyl-1H-pyrazol-4-yl)-2'-((cyclopropylmethyl)amino)-[2,4'-bipyridine]-6-carboxamide (1);
N-(3-carbamoyl-1-methyl-1H-pyrazol-4-yl)-6-(1H-pyrrol-1-yl)picolinamide (2);
4-(3-(2-(cyclopropylmethylamino)pyridin-4-yl)benzamido)-1-methyl-1H-pyrazole-3-carboxamide (3);
tert-butyl(6-((3-carbamoyl-1-methyl-1H-pyrazol-4-yl)carbamoyl)-[2,4'-bipyridin]-2'-yl)carbamate (4);
N-(3-carbamoyl-1-methyl-1H-pyrazol-4-yl)-2'-(cyclopropylmethylamino)-2,4'-bipyridine-4-carboxamide (5);
2'-amino-N-(3-carbamoyl-1-methyl-1H-pyrazol-4-yl)-[2,4'-bipyridine]-6-carboxamide (6);

N-(3-carbamoyl-1-methyl-1H-pyrazol-4-yl)-2'-(cyclopropylmethylamino)-3,4'-bipyridine-5-carboxamide (7);
N-(5-carbamoyl-1-methyl-1H-pyrazol-4-yl)-2'-(cyclopropylmethylamino)-2,4'-bipyridine-6-carboxamide (8);
N-(3-carbamoyl-1-methyl-1H-pyrazol-4-yl)-6-morpholinopicolinamide (9);
N-(3-carbamoyl-1-methyl-1H-pyrazol-4-yl)-6-(piperazin-1-yl)picolinamide (10);
N-(3-carbamoyl-1-methyl-1H-pyrazol-4-yl)-2,4'-bipyridine-6-carboxamide (11);
N-(3-carbamoyl-1-methyl-1H-pyrazol-4-yl)-[2,3'-bipyridine]-6-carboxamide (12);
N-(3-carbamoyl-1-methyl-1H-pyrazol-4-yl)-6-(3-methoxyphenyl)picolinamide (13);
N-(3-carbamoyl-1-methyl-1H-pyrazol-4-yl)-6-phenylpicolinamide (14);
N-(3-carbamoyl-1-methyl-1H-pyrazol-4-yl)-2'-((2-methoxyethyl)amino)-[2,4'-bipyridine]-6-carboxamide (15);
N-(3-carbamoyl-1-methyl-1H-pyrazol-4-yl)-2'-((2,2-difluoroethyl)amino)-[2,4'-bipyridine]-6-carboxamide (16);
N-(3-carbamoyl-1-methyl-1H-pyrazol-4-yl)-2'-(((tetrahydro-2H-pyran-4-yl)methyl)amino)-[2,4'-bipyridine]-6-carboxamide (17);
N-(3-carbamoyl-1-methyl-1H-pyrazol-4-yl)-2'-((2,2,2-trifluoroethyl)amino)-[2,4'-bipyridine]-6-carboxamide (18);
N-(3-carbamoyl-1-methyl-1H-pyrazol-4-yl)-2-(2-((cyclopropylmethyl)amino)pyridin-4-yl)pyrimidine-4-carboxamide (19);
N-(3-carbamoyl-1-methyl-1H-pyrazol-4-yl)-2'-methoxy-[2,3'-bipyridine]-6-carboxamide (20);
N-(3-carbamoyl-1-methyl-1H-pyrazol-4-yl)-6-(3-(trifluoromethoxy)phenyl)picolinamide (21);
N-(3-carbamoyl-1-methyl-1H-pyrazol-4-yl)-6-(thiophen-3-yl)picolinamide (22);
N-(3-carbamoyl-1-methyl-1H-pyrazol-4-yl)-6'-morpholino-[2,3'-bipyridine]-6-carboxamide (23);
N-(3-carbamoyl-1-methyl-1H-pyrazol-4-yl)-6-(3-(methylcarbamoyl)phenyl)picolinamide (24);
N-(3-carbamoyl-1-methyl-1H-pyrazol-4-yl)-6-(1-methyl-1H-pyrazol-4-yl)picolinamide (25);
N-(3-carbamoyl-1-methyl-1H-pyrazol-4-yl)-6-(1,1-dioxido-3,6-dihydro-2H-thiopyran-4-yl)picolinamide (26);
N-(3-carbamoyl-1-methyl-1H-pyrazol-4-yl)-6-(5,6-dihydro-2H-pyran-3-yl)picolinamide (27);
N-(3-carbamoyl-1-methyl-1H-pyrazol-4-yl)-6'-cyclopropyl-[2,3'-bipyridine]-6-carboxamide (28);
N-(3-carbamoyl-1-methyl-1H-pyrazol-4-yl)-5'-chloro-[2,3'-bipyridine]-6-carboxamide (29);
N-(3-carbamoyl-1-methyl-1H-pyrazol-4-yl)-6-(3,6-dihydro-2H-pyran-4-yl)picolinamide (30);
N-(3-carbamoyl-1-methyl-1H-pyrazol-4-yl)-4'-chloro-[2,3'-bipyridine]-6-carboxamide (31);
N-(3-carbamoyl-1-methyl-1H-pyrazol-4-yl)-1'-methyl-6'-oxo-1',2',3',6'-tetrahydro-[2,4'-bipyridine]-6-carboxamide (32);
N-(3-carbamoyl-1-methyl-1H-pyrazol-4-yl)-1'-methyl-1',2',5',6'-tetrahydro-[2,3'-bipyridine]-6-carboxamide (33);
2'-((cyclopropylmethyl)amino)-N-(1-methyl-3-(((1-methylpyrrolidin-3-yl)methyl)carbamoyl)-1H-pyrazol-4-yl)-[2,4'-bipyridine]-6-carboxamide (34);
2'-((cyclopropylmethyl)amino)-N-(1-methyl-3-((2-(pyrrolidin-1-yl)ethyl)carbamoyl)-1H-pyrazol-4-yl)-[2,4'-bipyridine]-6-carboxamide (35);
N-(3-(((1H-imidazol-2-yl)methyl)carbamoyl)-1-methyl-1H-pyrazol-4-yl)-2'-((cyclopropylmethyl)amino)-[2,4'-bipyridine]-6-carboxamide (36);
2'-((cyclopropylmethyl)amino)-N-(3-((5-(dimethylamino)pentyl)carbamoyl)-1-methyl-1H-pyrazol-4-yl)-[2,4'-bipyridine]-6-carboxamide (37);
2'-((cyclopropylmethyl)amino)-N-(1-methyl-3-((2-(pyridin-2-yl)ethyl)carbamoyl)-1H-pyrazol-4-yl)-[2,4'-bipyridine]-6-carboxamide (38);
2'-((cyclopropylmethyl)amino)-N-(1-methyl-3-(4-methylpiperazine-1-carbonyl)-1H-pyrazol-4-yl)-[2,4'-bipyridine]-6-carboxamide (39);
2'-((cyclopropylmethyl)amino)-N-(3-((3-(dimethylamino)propyl)carbamoyl)-1-methyl-1H-pyrazol-4-yl)-[2,4'-bipyridine]-6-carboxamide (40);
2'-((cyclopropylmethyl)amino)-N-(1-methyl-3-(morpholine-4-carbonyl)-1H-pyrazol-4-yl)-[2,4'-bipyridine]-6-carboxamide (41);
N-(3-(3-(aminomethyl)azetidine-1-carbonyl)-1-methyl-1H-pyrazol-4-yl)-2'-((cyclopropylmethyl)amino)-[2,4'-bipyridine]-6-carboxamide (42);
2'-((cyclopropylmethyl)amino)-N-(1-methyl-3-(pyrimidin-5-ylcarbamoyl)-1H-pyrazol-4-yl)-[2,4'-bipyridine]-6-carboxamide (43);
2'-((cyclopropylmethyl)amino)-N-(1-methyl-3-((2-(pyrazin-2-yl)ethyl)carbamoyl)-1H-pyrazol-4-yl)-[2,4'-bipyridine]-6-carboxamide (44);
2'-((cyclopropylmethyl)amino)-N-(3-(((1,1-dioxidotetrahydrothiophen-3-yl)methyl)carbamoyl)-1-methyl-1H-pyrazol-4-yl)-[2,4'-bipyridine]-6-carboxamide (45);
2'-((cyclopropylmethyl)amino)-N-(3-((3S,4S)-3-(dimethylamino)-4-hydroxypyrrolidine-1-carbonyl)-1-methyl-1H-pyrazol-4-yl)-[2,4'-bipyridine]-6-carboxamide (46);
2'-((cyclopropylmethyl)amino)-N-(1-methyl-3-((pyrimidin-4-ylmethyl)carbamoyl)-1H-pyrazol-4-yl)-[2,4'-bipyridine]-6-carboxamide (47);
N-(3-(((1,3,4-thiadiazol-2-yl)methyl)carbamoyl)-1-methyl-1H-pyrazol-4-yl)-2'-((cyclopropylmethyl)amino)-[2,4'-bipyridine]-6-carboxamide (48);
2'-((cyclopropylmethyl)amino)-N-(1-methyl-3-(((1-methylpiperidin-3-yl)methyl)carbamoyl)-1H-pyrazol-4-yl)-[2,4'-bipyridine]-6-carboxamide (49);
N-(3-((2-(1H-pyrazol-1-yl)ethyl)carbamoyl)-1-methyl-1H-pyrazol-4-yl)-2'-((cyclopropylmethyl)amino)-[2,4'-bipyridine]-6-carboxamide (50); and
2'-((cyclopropylmethyl)amino)-N-(1-methyl-3-((tetrahydrofuran-3-yl)carbamoyl)-1H-pyrazol-4-yl)-[2,4'-bipyridine]-6-carboxamide (51);
or a pharmaceutically acceptable salt or stereoisomer thereof A compound of the instant invention is selected from:
N-(3-carbamoyl-1-methyl-1H-pyrazol-4-yl)-2'-((cyclopropylmethyl)amino)-[2,4'-bipyridine]-6-carboxamide (1);
N-(3-carbamoyl-1-methyl-1H-pyrazol-4-yl)-[2,3'-bipyridine]-6-carboxamide (12);
N-(3-carbamoyl-1-methyl-1H-pyrazol-4-yl)-2'-((2-methoxyethyl)amino)-[2,4'-bipyridine]-6-carboxamide (15);
N-(3-carbamoyl-1-methyl-1H-pyrazol-4-yl)-2'-((2,2-difluoroethyl)amino)-[2,4'-bipyridine]-6-carboxamide (16);
N-(3-carbamoyl-1-methyl-1H-pyrazol-4-yl)-2'-((2,2,2-trifluoroethyl)amino)-[2,4'-bipyridine]-6-carboxamide (18);
N-(3-carbamoyl-1-methyl-1H-pyrazol-4-yl)-6-(thiophen-3-yl)picolinamide (22);
N-(3-carbamoyl-1-methyl-1H-pyrazol-4-yl)-6'-cyclopropyl-[2,3'-bipyridine]-6-carboxamide (28);
N-(3-carbamoyl-1-methyl-1H-pyrazol-4-yl)-1'-methyl-6'-oxo-1',2',3',6'-tetrahydro-[2,4'-bipyridine]-6-carboxamide (32);

N-(3-(3-(aminomethyl)azetidine-1-carbonyl)-1-methyl-1H-pyrazol-4-yl)-2'-((cyclopropylmethyl)amino)-[2,4'-bipyridine]-6-carboxamide (42); and 2'-((cyclopropylmethyl)amino)-N-(1-methyl-3-(((1-methylpiperidin-3-yl)methyl)carbamoyl)-1H-pyrazol-4-yl)-[2,4'-bipyridine]-6-carboxamide (49);

or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted.

This invention is also intended to encompass pro-drugs of the compounds disclosed herein. A prodrug of any of the compounds can be made using well known pharmacological techniques.

When any variable (e.g. $R_1$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

In the compounds of Formulas I-III, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formulas I-III. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formulas I-III can be prepared without undue experimentation by conventional techniques well known to those skilled in the art or by processes analogous to those described in the Scheme and Examples herein using appropriate isotopically-enriched reagents and/or intermediates.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "($C_1$-$C_{10}$)alkyl" is defined to include groups having 1, 2, 3, 4, 5, 6, 7, 8, 9 or 10 carbons in a linear or branched arrangement. For example, "($C_1$-$C_{10}$)alkyl" specifically includes methyl, ethyl, n-propyl, i-propyl, n-butyl, t-butyl, i-butyl, pentyl, hexyl, heptyl, octyl, nonyl, decyl, and so on.

The term "cycloalkyl" means a monocyclic saturated aliphatic hydrocarbon group having the specified number of carbon atoms. For example, $C_3$-$C_8$, as in "($C_3$-$C_8$)cycloalkyl" is defined to include groups having 3, 4, 5, 6, 7 or 8 carbons which includes a circular arrangement.

For example, "($C_3$-$C_8$)cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "($C_2$-$C_{10}$)alkenyl" means an alkenyl radical having from 2 to 10 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "($C_2$-$C_{10}$)alkynyl" means an alkynyl radical having from 2 to 10 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring. In one embodiment of Formulas I-III, aryl is independently selected from phenyl, naphthyl, tetrahydro-naphthyl, indanyl and biphenyl optionally substituted with one to three substituents independently selected from $R_a$. In another embodiment of Formulas I-III, aryl is independently selected from phenyl, naphthyl, tetrahydro-naphthyl, indanyl and biphenyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes heteroaryls, as well as dihydro and tetrathydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In one embodiment of Formulas I-III, heterocyclyl is independently selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof, optionally substituted with one to three substituents independently selected from $R_a$.

In another embodiment of Formulas I-III, heterocyclyl is independently selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl and thiomorpholinyl.

In another embodiment of Formulas I-III, heterocyclyl is independently selected from carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl and thiomorpholinyl.

As appreciated by those of skill in the art, "halo" or "halogen" as used herein is intended to include chloro (Cl), fluoro (F), bromo (Br) and iodo (I).

In an embodiment of Formula I and II, Ring A is aryl, heteroaryl or heterocycle optionally substituted with one to three substituents independently selected from $R_1$.

In another embodiment of Formula I and II, Ring A is phenyl, benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl and thiomorpholinyl, which are optionally substituted with one to three substituents independently selected from $R_1$.

In another embodiment of Formula I and II, Ring A is phenyl, pyrazinyl, pyrazolyl, pyridyl, pyrimidyl, thienyl, piperazinylfuranyl, pyrrolozinyl, pyrrolidinyl, oxazolyl, thiazolyl, imidazolyl, isozazolyl, oxadiazolyl, triazolyl, thiadiazolyl, piperidinyl, pyridazinyl. and morpholinyl, which are optionally substituted with one to three substituents independently selected from $R_1$.

In another embodiment of Formula I and II, Ring A is phenyl, pyrazinyl, pyrazolyl, pyridyl, pyrimidyl, thienyl, piperazinyl, furanyl, pyrrolozinyl, pyrrolidinyl, oxazolyl, thiazolyl, imidazolyl, isozazolyl, oxadiazolyl, triazolyl, thiadiazolyl, piperidinyl, pyridazinyl.
and morpholinyl, which are optionally substituted with one to three substituents independently selected from $R_a$.

In another embodiment of Formula I and II, Ring A is phenyl, pyrazinyl, pyrazolyl, pyridyl, pyrimidyl, thienyl, piperazinylfuranyl, pyrrolozinyl, pyrrolidinyl, oxazolyl, thiazolyl, imidazolyl, isozazolyl, oxadiazolyl, triazolyl, thiadiazolyl, piperidinyl, pyridazinyl. and morpholinyl, which are optionally substituted with one to three substituents independently selected from $R_b$.

In an embodiment of Formula I, II and III, $R_1$ is independently selected from: H, oxo, $(C=O)_a(C_1-C_{10})$alkyl, $(C=O)_a$-aryl, $CO_2H$, halo, OH, $O_b(C_1-C_6)$fluoroalkyl, $(C=O)_aNR_5R_6$, CN, $(C=O)_a(C_3-C_8)$cycloalkyl and $(C=O)_aO_b$-heterocyclyl, said alkyl, aryl, cycloalkyl, and heterocyclyl are optionally substituted with one or more substituents selected from $R_a$.

In another embodiment of Formula I, II and III, $R_1$ is independently selected from: H, oxo, $(C_1-C_6)$alkyl, aryl, $CO_2H$, halo, OH, $(C_1-C_6)$fluoroalkyl, $NR_5R_6$, CN, $(C_3-C_8)$cycloalkyl and heterocyclyl, said alkyl, aryl, cycloalkyl, and heterocyclyl are optionally substituted with one to three substituents selected from $R_a$.

In another embodiment of Formula I, II and III, $R_1$ is independently selected from: H and $NR_5R_6$.

In another embodiment of Formula I, II and III, $R_1$ is independently selected from: H and $N(R_a)_2$.

In another embodiment of Formula I, II and III, $R_1$ is independently selected from: H and $N(R_b)_2$.

In another embodiment of Formula I, II and III, $R_1$ is:

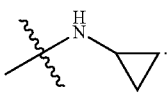

In another embodiment of Formula I, II and III, $R_1$ is H.

In an embodiment of Formula I, $R_2$ and $R_3$ are independently selected from: H and $C_1-C_6$ alkyl, optionally substituted with one or more substituents selected from $R_1$; or $R_2$ and $R_3$ can be taken together with the nitrogen to which they are attached to form a monocyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R_1$.

In another embodiment of Formula I, $R_2$ and $R_3$ are independently selected from: H and $C_1-C_6$ alkyl, optionally substituted with one to three substituents selected from $R_a$; or $R_2$ and $R_3$ can be taken together with the nitrogen to which they are attached to form a monocyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R_a$.

In another embodiment of Formula I, $R_2$ and $R_3$ are independently selected from: H and $C_1-C_6$ alkyl, optionally substituted with one to three substituents selected from $R_b$; or $R_2$ and $R_3$ can be taken together with the nitrogen to which they are attached to form a monocyclic heterocycle with 3-7 members in each ring and optionally containing, in addition to the nitrogen, one or two additional heteroatoms selected from N, O and S, said monocyclic or bicyclic heterocycle optionally substituted with one to three substituents selected from $R_b$.

In an embodiment of Formula I and II, $R_4$ is selected from $(C_1-C_6)$alkyl optionally substituted with OH, methoxy and halogen.

In another embodiment of Formula I and II, $R_4$ is selected from $(C_1-C_4)$alkyl.

In another embodiment of Formula I and II, $R_4$ is methyl.

In an embodiment of Formula I, II and III, $R_5$ and $R_6$ are independently selected from: H, $(C=O)_a(C_1-C_{10})$alkyl, $(C=O)_a(C_3-C_8)$cycloalkyl, $(C=O)_a$-aryl, $(C=O)_a$-heterocyclyl and $(C=O)_aNR_{a2}$.

In another embodiment of Formula I, II and III, $R_5$ and $R_6$ are independently selected from: H, $(C=O)_a(C_1-C_6)$alkyl, $(C=O)_a(C_3-C_6)$cycloalkyl, $(C=O)_a$-phenyl, $(C=O)_a$-heterocyclyl and $(C=O)_aNR_{a2}$.

In another embodiment of Formula I, II and III, $R_5$ and $R_6$ are independently selected from: H, $(C=O)_a(C_1-C_4)$alkyl, $(C=O)_a(C_3)$cycloalkyl, $(C=O)_a$-phenyl, and $(C=O)_aNR_{b2}$.

In an embodiment of Formula I, II and III, $R_a$ is independently selected from $R_b$, OH, $(C_1-C_6)$alkoxy, halogen, cyclopropyl, $CO_2H$, CN, $O_a(C=O)_b(C_1-C_6)$alkyl, oxo, and $N(R_b)_2$.

In another embodiment of Formula I, II and III, $R_a$ is independently selected from $R_b$, OH, $(C_1-C_4)$alkoxy, halogen, cyclopropyl, $CO_2H$, CN, $(C_1-C_4)$alkyl, oxo, and $N(R_b)_2$.

In another embodiment of Formula I, II and III, $R_a$ is independently selected from $R_b$, $(C_1-C_6)$alkoxy, cyclopropyl, $CO_2H$, CN, $O_a(C=O)_b(C_1-C_6)$alkyl, and $N(R_b)_2$.

In an embodiment of Formula I, II and III, $R_b$ is independently selected from H and methyl.

Included in the instant invention is the free form of compounds of Formulas I-III, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formulas I-III. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

UTILITY

According to yet another embodiment, the present invention provides a method of treating or reducing the severity of a disease in a patient by using a compound of Formulas I-III as described above, wherein said disease is selected from IRAK4 mediated pathologies, such as rheumatoid arthritis, multiple sclerosis, sepsis, osteoarthritis, inflammatory bowel disease, Parkinson's disease, cardiac contractile dysfunction, type I diabetes, type II diabetes or familial cold autoinflammatory syndrome, allergic disease, cancer, psoriasis, asthma or graft rejection.

The compounds of the invention find use in a variety of applications. As will be appreciated by those skilled in the art, the kinase activity of IRAK-4 may be modulated in a variety of ways; that is, one can affect the phosphorylation/activation of IRAK-4 either by modulating the initial phosphorylation of the protein or by modulating the autophosphorylation of the other active sites of the protein. Alternatively, the kinase activity of IRAK-4 may be modulated by affecting the binding of a substrate of IRAK-4 phosphorylation.

The compounds of the invention are used to treat or prevent inflammation related diseases. Disease states which can be treated by the methods and compositions provided herein include, but are not limited to, cancer, autoimmune disease, viral disease, fungal disease, neurological/neurodegenerative disorders, arthritis, inflammation, anti-proliferative (e.g. ocular retinopathy), neuronal, alopecia, cardiovascular disease, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For topical use, creams, ointments, jellies, solutions or suspensions, etc., containing the compound of Formulas I-III are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, age, weight, sex; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 10,000 mg. Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg. Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter refered to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention.

The instant compounds are also useful in combination with other therapeutic agents. Combinations of the presently disclosed compounds with therapeutic agents are within the scope of the invention. A person of ordinary skill in the art would be able to discern which combinations of agents would be useful based on the particular characteristics of the drugs and the pathologies involved. The instant compounds are also useful in combination with known therapeutic agents.

The instant compounds are useful in combination with a known anti-inflammatory agent. In one embodiment, the anti-inflammatory agent is a nonsteroidal anti-inflammatory drug (NSAID). In one embodiment, the NSAID is selected from the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, and a mixture thereof.

In another embodiment, the NSAID is a selective COX-2 inhibitor. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272, and 5,932,598, all of which are hereby incorporated by reference.

Compounds that have been described as specific inhibitors of COX-2 and are therefore useful in the present invention include, but are not limited to: parecoxib, CELEBREX® and BEXTRA® or a pharmaceutically acceptable salt thereof.

The instant compounds are useful in combination with a known anti-cancer agent. Combinations of the presently disclosed compounds with anti-cancer agents are within the scope of the invention. Examples of such anti-cancer agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

In one embodiment, the anti-cancer agent is selected from the group consisting of abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin ®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection ®); cyclophosphamide (Cytoxan Table®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (dromostanolone®); dromostanolone propionate (masterone injection®); Elliott's B Solution (Elliott's B Solution®); epirubicin (Ellence®); Epoetin alfa (epogen®); erlotinib (Tarceva®); estramustine (Emcyt®); etoposide phosphate (Etopophos®); etoposide, VP-16 (Vepeside®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovoring, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®)); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®); a pharmaceutically acceptable salt thereof, and a mixture thereof.

Any one or more of the specific dosages and dosage schedules of the compounds of the instant invention, may also be applicable to any one or more of the therapeutic agents to be used in the combination treatment (hereinafter refered to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The compounds of the instant invention are useful for the treatment and/or reducing the severity of rheumatoid arthritis.

The compounds of the instant invention are useful for the treatment and/or reducing the severity of inflammatory bowel disease.

The compounds of the instant invention are useful for the treatment and/or reducing the severity of cancer.

The compounds of the instant invention are useful for the treatment of rheumatoid arthritis.

The compounds of the instant invention are useful for the treatment of inflammatory bowel disease.

The compounds of the instant invention are useful for the treatment of cancer.

Further included within the scope of the invention is a method for treating an inflammatory disease which comprises administering to a mammal in need thereof a therapeutically effective amount of a compound of the instant invention.

Further included within the scope of the invention is a method for treating an inflammatory disease which comprises administering to a mammal in need thereof a therapeutically effective amount of a compound of the instant invention wherein the inflammatory disease is selected from rheumatoid arthritis, inflammatory bowel disease and cancer.

Further included within the scope of the invention is a method of treating an inflammatory disease which comprises administering a therapeutically effective amount of a compound of the instant invention in combination with a second therapeutic agent.

Further included within the scope of the invention is a method of treating an inflammatory disease which comprises administering a therapeutically effective amount of a compound of the instant invention in combination with a second therapeutic agent, wherein the second therapeutic agent is selected from an anti-cancer agent and an anti-inflammatory agent.

Abbreviations used in the description of the chemistry and in the Examples that follow are: $CDCl_3$ (chloroform-d); DCM (dichloromethane); DMF (N,N-dimethylformamide); DMSO (dimethyl sulfoxide); EtOAc (ethyl acetate); EtOH (ethanol); HPLC (high-performance liquid chromatography); LCMS (liquid chromatograph-mass spectrometer); MeOH (methanol); NMR (nuclear magnetic resonance); Pd(dppf) ([1,1-bis(diphenylphosphino)ferrocene]palladium); $Pd(Ph_3)_4$ (palladium(0)tetrakis-triphenylphosphine); $POCl_3$ (phosphorous oxychloride); THF (tetrahydrofuran); TFA (trifluoroacteic acid); BOC (t-butoxycarbonyl); DMAP (4-dimethylaminopyridine); EDC (N-ethyl-N'-(3-dimethyl-aminopropyl)carbodiimide); HOBT (hydroxybenzotriazole); LC/MS (liquid chromatograph-mass spectrometer); MeCN (acetonitrile); TLC (thin layer chromatography); $CD_3OD$ (methanol-d); TBTU (O-(benzotriazol-1-yl)-N,N,N',N'-tetramethyluronium tetrafluoroborate).

General Synopsis of Reaction Schemes

The following General Reaction Scheme A-I provides useful details for preparing the instant compounds. The requisite intermediates are in some cases commercially available or can be prepared according to literature procedures. The illustrative General Reaction Scheme below, therefore, are not limited by the compounds listed or by any particular substituents employed for illustrative purposes. Substituent labeling (i.e. R groups) as shown in the General Reaction Scheme does not necessarily correlate to that used in the claims and often, for clarity, a single substituent is shown attached to the compound where multiple substituents are allowed under the definitions of Formula I-III hereinabove.

As illustrated in Scheme A-I, a nitropyrazine A-1 can be alkylated under basic condtions to generate the corresponding N-alkyl deriviative A-2. The derivative can then be converted to the corresponding amine A-3, in this case, by hydrogenation. The newly formed amine can then be coupled with a carboxylic acid, in this case an aryl carboxylic acid to generate an amide such as compound A-4.

General Reaction Scheme A-I

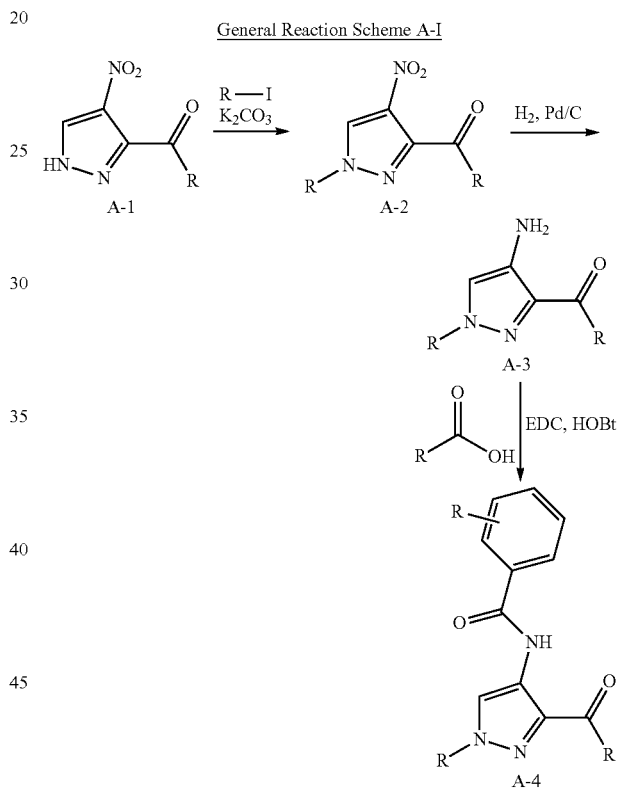

The compounds of this invention may be prepared by employing reactions as shown in the following Reaction Schemes, in addition to other standard manipulations that are known in the literature or exemplified in the experimental procedures.

Synopsis of Reaction Schemes

The following Reaction schemes provide useful details for preparing the instant compounds. The requisite intermediates are in some cases commercially available or can be prepared according to literature procedures.

As illustrated in the following schemes, a nitropyrazine 1 can be alkylated under basic condtions to generate the corresponding N-methyl derivative 2. The derivative can then be converted to the corresponding amine 3, in this case, by hydrogenation. The newly formed amine can then be coupled with a carboxylic acid, in this case an aryl carboxylic acid to generate an amide such as compound 5. Alternatively, an aryl bromide such as 6 can be cross-coupled to an aryl pinacol bornate ester to provide a biaryl such as 8. The biaryl can then be alkylated on the amine to give an N-alkyl derivative such as 10. The ester can be hydrolyzed to the acid, in this case using sodium hydroxide. The acid can then be coupled to an amine as described for compound 5. Removal of protecting groups, in this case the tert-butoxylcarbonyl from the amine will give the desired compounds. Additionally, relevant compounds can be made by derivitizing intermediates such as 5, in one example by reaction with pyrrole to provide Example 2.

Determination of IRAK4 Kinase Activity

The kinase activity of IRAK4 is determined by its ability to catalyze the phosphorylation of a fluorescent polypeptide substrate. The extent of phosphorylation is measured using IMAP technology (Molecular Devices) where the phosphorylated fluorescent substrate binds to the large M(III)-based nanoparticles which reduces the rotational speed of the substrate and thus increases its fluorescent polarization (FP).

Specific compounds of the instant invention were tested in the assay described above and were found to have $IC_{50}$ values of ≤20 μM against substrate.

Procedure: A 20 μl reaction mixture contains 10 mM TriHCl, pH 7.2, 0.5 nM GST tagged IRAK4 (SignalChem), 100 nM fluorescent peptide substrate (RP7030, Molecular Devices), 100 μM ATP, 1 mM DTT, 1 mM $MgCl_2$, and 0.01% Tween 20. The reaction is initiated by the addition of ATP. After incubation for 30 minutes at 25° C., 60 μl of Progressive IMAP Reagent (Molecular Devices) is added to stop the reaction. Change in RP7030's FP is determined by a FP reader (Analyst HT, LJL BioSystems).

Synthesis of Intermediates

LCMS Conditions: Agilent SBC (3.0×50 mm), solvent A: $H_2O$-0.1% TFA; solvent B: MeCN-0.1% TFA; GRADIENT TABLE: 0 min: 10% B, 0.3 min: 10% B, 1.5 min: 95% B, 2.70 min: 95% B, 2.76 min: 10% B, stop time 3.60 min.

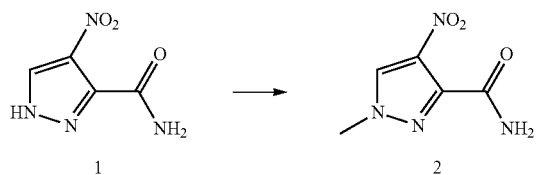

In a round bottomed flask, 4-nitro-1H-pyrazole-3-carboxamide (10 g, 63.7 mmol), potassium carbonate (26.4 g, 191 mmol) and methyl iodide (15.92 mL, 255 mmol) were combined in 200 mL dry N,N-dimethylformamide and stirred 18 hours at room temperature. The reaction mixture was then concentrated, diluted with ethyl acetate, washed with water and brine, dried over sodium sulfate and concentrated. The crude mixture was purified by column chromatography in 25% ethyl acetate in hexanes to yield 2.37 g (12.8 mmol, 20%) of 4-nitro-1-methyl-1H-pyrazole-3-carboxamide. 3.66 g (19.76 mmol, 31%) of regioisomer 1-methyl-4-nitro-1H-pyrazole-5-carboxamide was also obtained. LCMS 0.38 min, M/Z=171 [M+H].

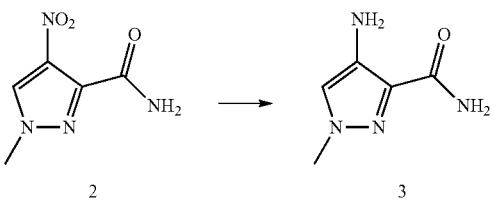

In a PARR reaction vessel, 1-methyl-4-nitro-1H-pyrazole-3-carboxamide (2.37 g, 12.8 mmol) was dissolved in ethanol. 10% Palladium on carbon (0.681 g, 0.640 mmol) was added, the vessel was pressurized (40 psi) with hydrogen and the mixture was shaken for 5 hours. The mixture was filtered through celite and concentrated to obtain 1.82 g (11.7 mmol, 92%) of 4-amino-1-methyl-1H-pyrazole-3-carboxamide. $^1$H NMR (DMSO-d6) 7.13 (br s, 1H), 7.10 (s, 1H), 6.92 (br s, 1H), 4.61 (s, 2H), 3.70 (s, 3H); LCMS 0.27 min, M/Z=141 [M+H].

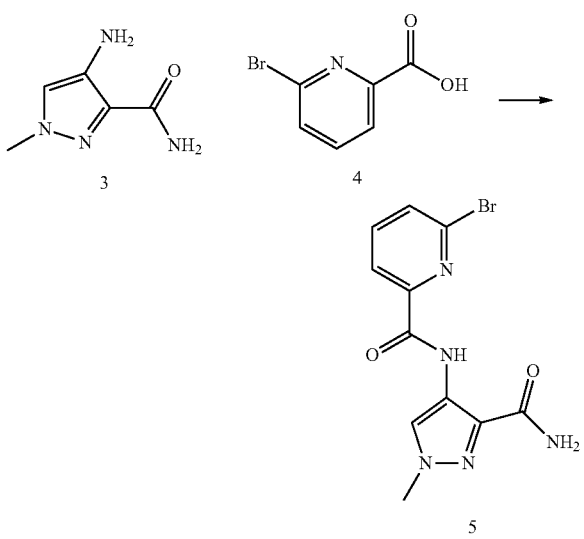

In a round bottomed flask was combined 0.178 mL (1.28 mmol) of triethylamine, 131 mg (0.853 mmol) of 1H-benzo[d][1,2,3]triazol-1-ol hydrate, 84 mg (0.597 mmol) of 4-amino-1-methyl-1H-pyrazole-3-carboxamide and 86.2 mg (0.427 mmol) of 6-bromopicolinic acid in 2 mL of dry N,N-dimethylformamide at room temperature. The mixture was stirred for ten minutes at room temperature, then added 164 mg (0.853 mmol) N1-((ethylimino)methylene)-N3,N3-dimethylpropane-1,3-diamine hydrochloride and the reaction mixture was stirred for 5 hours. The mixture was diluted with ethyl acetate, washed with water and brine, dried over sodium sulfate and concentrated to obtain 118 mg (0.362 mmol) of crude 6-bromo-N-(3-carbamoyl-1-methyl-1H-pyrazol-4-yl)picolinamide. LCMS 1.27 min, M/Z=324 [M+H].

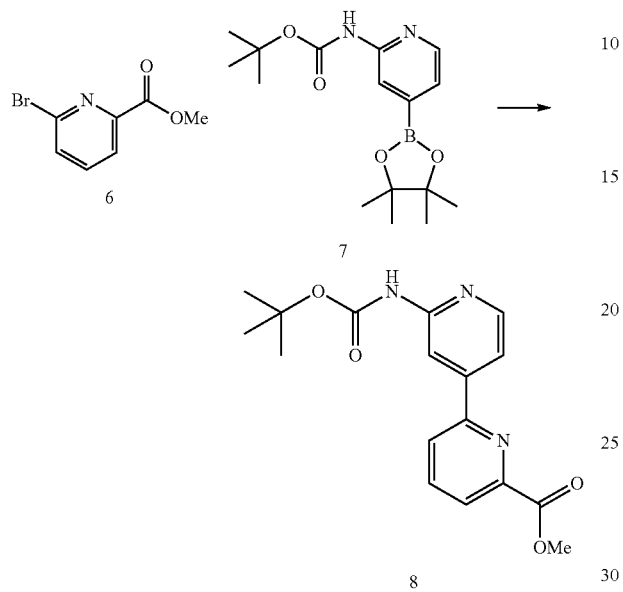

In a microwave vial, tert-butyl(4-(4,4,5,5-tetramethyl-1,3,2-dioxaborolan-2-yl)pyridin-2-yl)carbamate (326 mg, 1.02 mmol), methyl 6-bromopicolinate (200 mg, 0.926 mmol), potassium carbonate (1.85 mL, 1.85 mmol) and 1,1'-bis(diphenylphosphino)ferrocene dichloro palladium (II) dichloromethane complex (67.7 mg, 0.093 mmol) were combined in 6 mL of dry tetrahydrofuran, degassed for ten minutes, then sealed and heated to 70° C. for 3 hours. The reaction mixture was cooled to room temperature, diluted with ethyl acetate, washed with water and brine, dried over sodium sulfate and concentrated. The crude mixture was then purified via column chromatography in a 0-45% ethyl acetate in hexanes gradient to yield 183 mg (0.556 mmol, 60%) of the product, methyl 2'-((tert-butoxycarbonyl)amino)-[2,4'-bipyridine]-6-carboxylate. LCMS 2.00 min, M/Z=330 [M+H].

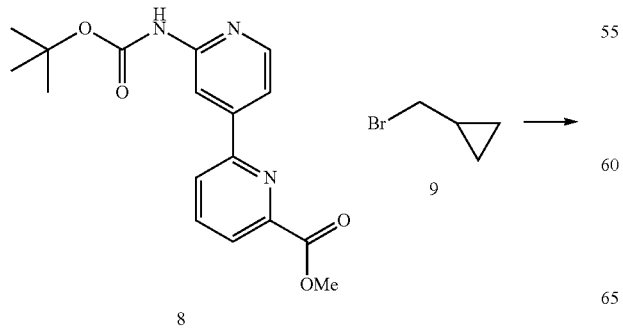

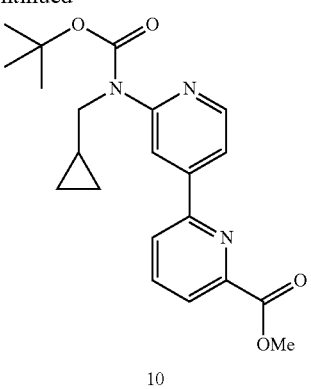

In a round bottomed flask methyl 2'-((tert-butoxycarbonyl)amino)-[2,4'-bipyridine]-6-carboxylate (183 mg, 0.557 mmol), (bromomethyl)cyclopropane (0.107 mL, 1.11 mmol) and cesium carbonate (544 mg, 1.671 mmol) were combined in 1 mL of dry N,N-dimethylformamide and heated to 70° C. for 18 hours. After cooling to room temperature the mixture was diluted with ethyl acetate, washed with water and brine, dried over sodium sulfate and concentrated. The crude mixture was purified by column chromatography in 0-30% ethyl acetate in hexanes to give 87.3 mg (0.227 mmol, 40%) of the product, methyl 2'-((tert-butoxycarbonyl)(cyclopropylmethyl)amino)-[2,4'-bipyridine]-6-carboxylate. LCMS 2.57 min, M/Z=384 [M+H].

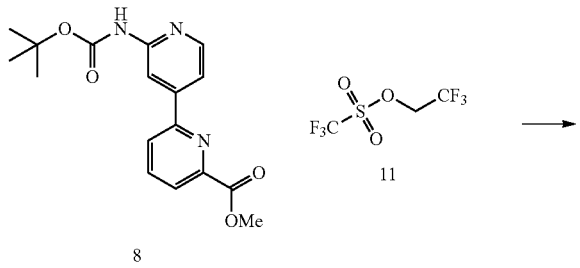

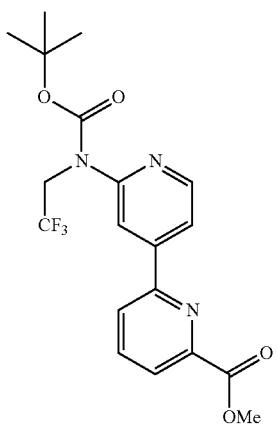

In a round bottomed flask 70 mg (0.213 mmol) methyl 2'-((tert-butoxycarbonyl)amino)-[2,4'-bipyridine]-6-carboxylate was dissolved in 2 mL dry N,N-dimethylformamide and cooled to 0° C. 12.8 mg (0.319 mmol) of sodium hydride was added and the reaction mixture was stirred for five minutes. 2,2,2-Trifluoroethyl trifluoromethanesulfonate (0.092 mL, 0.638 mmol) was then added and the reaction was stirred and allowed to warm slowly to room temperature overnight. The reaction was quenched with sodium bicarbonate solution, diluted with ethyl acetate, washed with water and brine, dried over sodium sulfate and concentrated. 41.8 mg (0.101 mmol) of crude methyl 2'-((tert-butoxycarbonyl)(2,2,2-trifluoroethyl)amino)-[2,4'-bipyridine]-6-carboxylate was obtained. LCMS 1.91 min, M/Z=412 [M+H].

In a round bottomed flask, methyl 2'-((tert-butoxycarbonyl)(cyclopropylmethyl)amino)-[2,4'-bipyridine]-6-carboxylate (200 mg, 0.522 mmol) was dissolved in 4 mL of methanol. A 1 M sodium hydroxide solution was added (0.574 mL, 0.574 mmol) and the reaction mixture was heated to 50° C. for 3.5 h. The reaction was cooled to room temperature and concentrated. The crude reaction mixture was dissolved in water and 1 M hydrochloric acid was added. The mixture was concentrated to obtain 127 mg (0.343 mmol) of crude 2'-((tert-butoxycarbonyl)(cyclopropylmethyl)amino)-[2,4'-bipyridine]-6-carboxylic acid that was used without further purification. LCMS 2.32 min, M/Z=370 [M+H].

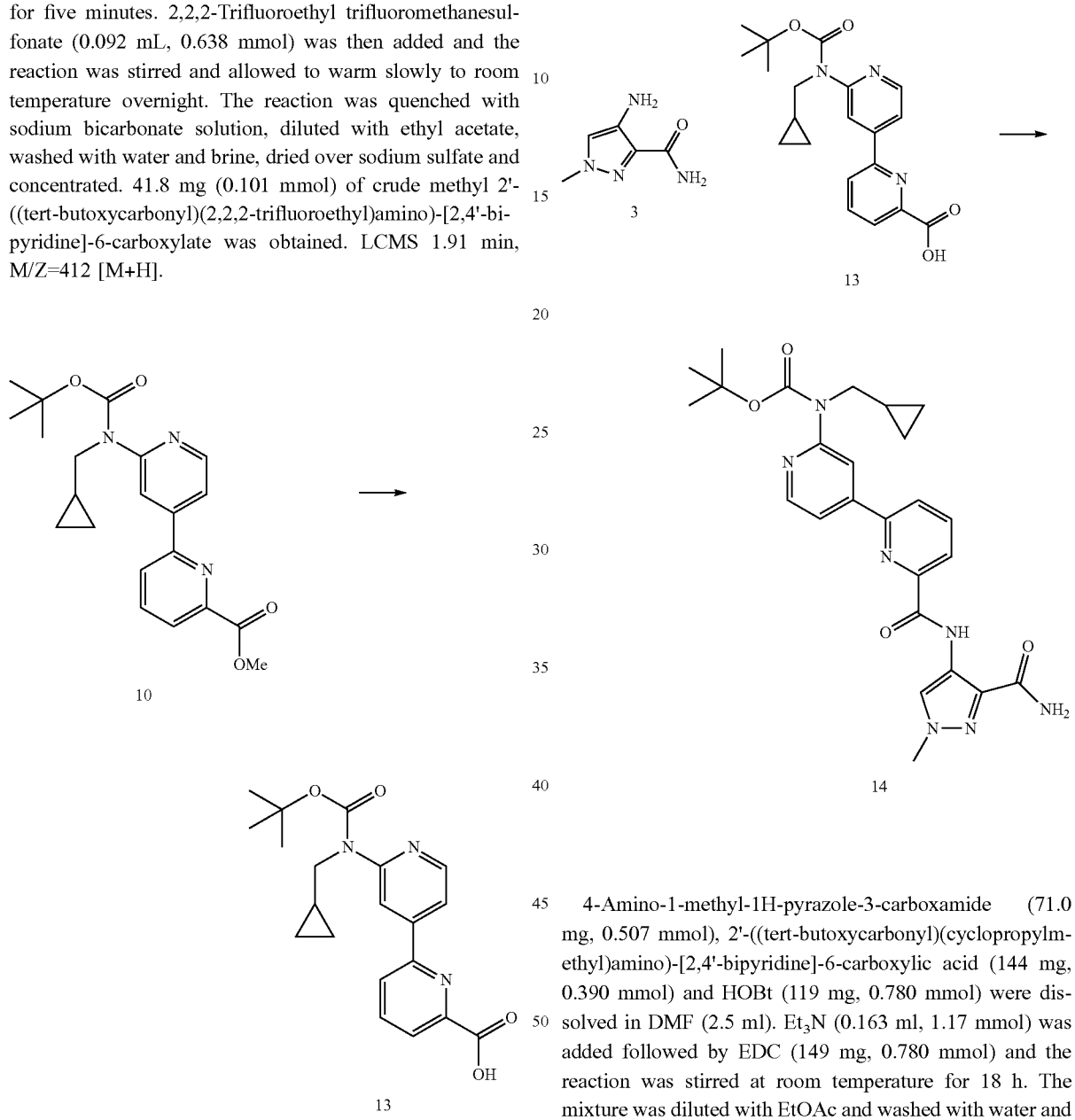

4-Amino-1-methyl-1H-pyrazole-3-carboxamide (71.0 mg, 0.507 mmol), 2'-((tert-butoxycarbonyl)(cyclopropylmethyl)amino)-[2,4'-bipyridine]-6-carboxylic acid (144 mg, 0.390 mmol) and HOBt (119 mg, 0.780 mmol) were dissolved in DMF (2.5 ml). Et$_3$N (0.163 ml, 1.17 mmol) was added followed by EDC (149 mg, 0.780 mmol) and the reaction was stirred at room temperature for 18 h. The mixture was diluted with EtOAc and washed with water and brine, dried (MgSO$_4$), filtered and concentrated. The residue was purified by preparative TLC on silica gel, eluting with CH$_2$Cl$_2$/MeOH/NH$_3$ to give tert-butyl (6-((3-carbamoyl-1-methyl-1H-pyrazol-4-yl)carbamoyl)-[2,4'-bipyridin]-2'-yl)(cyclopropylmethyl)carbamate (125 mg, 0.254 mmol, 65% yield) as a white solid.

$^1$H NMR (DMSO-d6) 8.52 (m, 1H), 8.42 (s, 1H), 8.36-8.31 (m, 2H), 8.25-8.15 (m, 3H). 7.74 (s, 1H), 7.56 (s, 1H), 3.93 (s, 3H), 3.83 (d, J=6.8 Hz, 2H), 1.45 (s, 9H), 1.17 (m, 1H), 0.41-0.36 (m, 2H), 0.22-0.19 (m, 2H); LCMS 2.37 min, M/Z=492 [M+H].

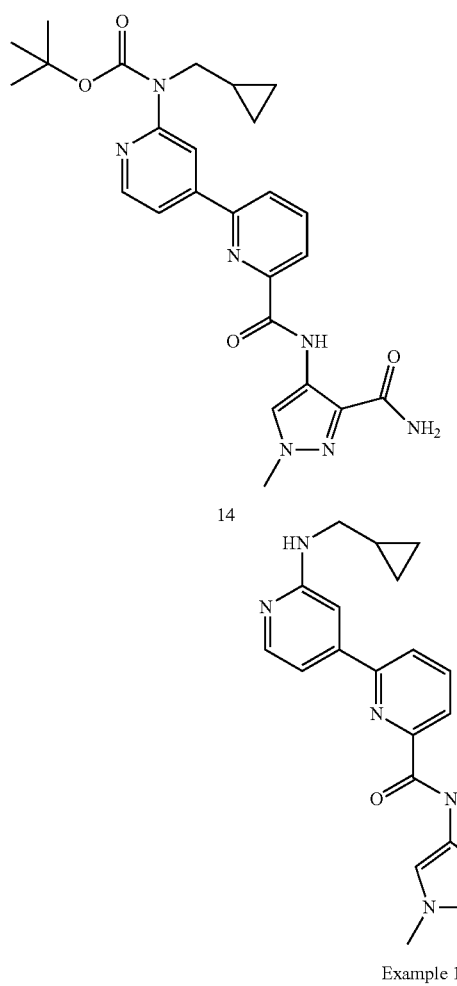

Example 1

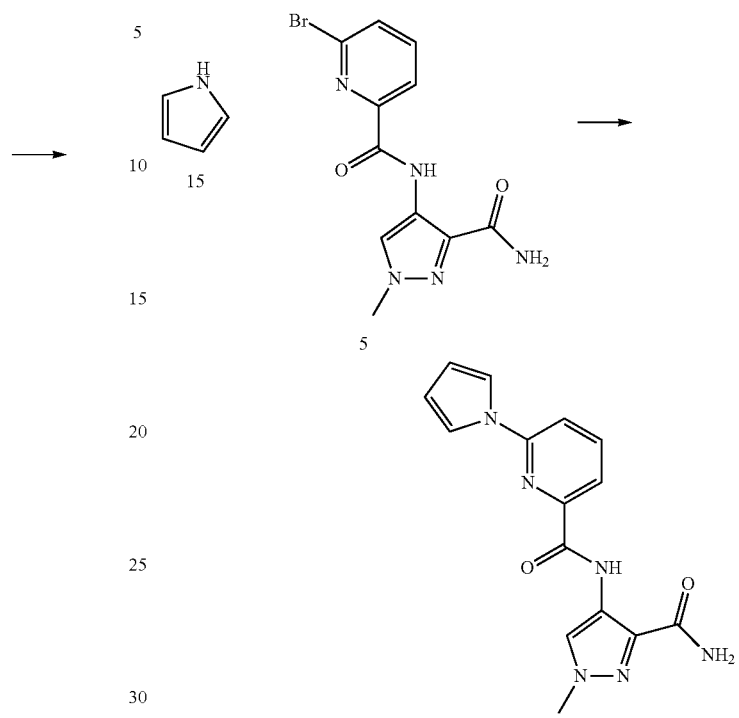

Example 2 bamoyl-1-methyl-1H-pyrazol-4-yl)-2'-((cyclopropylmethyl)amino)-[2,4'-bipyridine]-6-carboxamide (Example 1).

In a round bottomed flask, 81.1 mg (0.165 mmol) of tert-butyl(6-((3-carbamoyl-1-methyl-1H-pyrazol-4-yl)carbamoyl)-[2,4'-bipyridin]-2'-yl)(cyclopropylmethyl)carbamate was dissolved in 3 mL of trifluoroacetic acid and stirred at room temperature for 7 hours. The reaction mixture was concentrated to yield 82.5 mg (0.211 mmol) of N-(3-car- 6-Bromo-N-(3-carbamoyl-1-methyl-1H-pyrazol-4-yl)picolinamide (70 mg, 0.216 mmol), pyrrole (0.015 mL, 0.216 mmol) and potassium carbonate (90 mg, 0.648 mmol) were dissolved in N,N-dimethylformamide. The vessel was sealed and heated to 120° C. for 2 days. The mixture was diluted with ethyl acetate, washed with water and brine and concentrated. The residue was purified via preparative TLC in 50% ethyl acetate in hexanes to give the product, N-(3-carbamoyl-1-methyl-1H-pyrazol-4-yl)-6-(1H-pyrrol-1-yl)picolinamide (Example 2).

The following examples were synthesized according to the representative procedures stated above:

| Example | Structure | IRAK4 IC$_{50}$ (nM) | MS m/z & HPLC retention time | NMR |
|---|---|---|---|---|
| 1 | 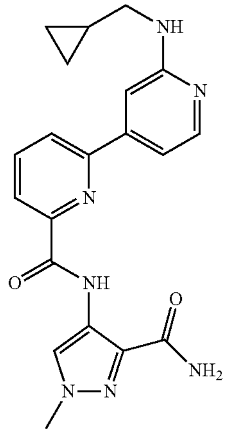 [SMILES: Cn1cc(NC(=O)c2cccc(-c3ccnc(NCC4CC4)c3)n2)c(C(N)=O)n1] | 74 | 392 [M + H]+, 1.8 min | 400 MHz (DMSO-d6) 8.42 (s, 1H), 8.39 (br s, 1H), 8.31-8.26 (m, 2H), 8.07 (d, 1H), 7.84 (s, 1H), 7.76 (d, 1H), 7.47 (s, 1H), 3.94 (s, 3H), 1.16 (m, 1H), 0.56-0.51 (m, 2H), 0.34-0.32 (m, 2H) |

| Example | Structure | IRAK4 IC$_{50}$ (nM) | MS m/z & HPLC retention time | NMR |
|---|---|---|---|---|
| 2 | 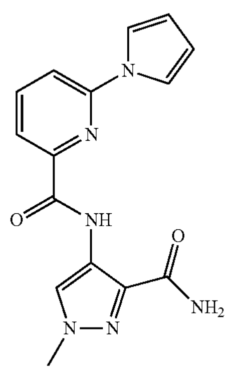 [SMILES: Cn1cc(NC(=O)c2cccc(-n3cccc3)n2)c(C(N)=O)n1] | 649 | 311 [M + H]+, 1.8 min | 400 MHz (CD$_3$OD) 11.70 (s, 1H), 8.33 (d, 1H), 8.16 (m, 1H), 7.60-7.95 (m, 3H), m 7.35 (d, 1H), 6.84 (d, 1H), 3.96 (s, 3H) |
| 3 | 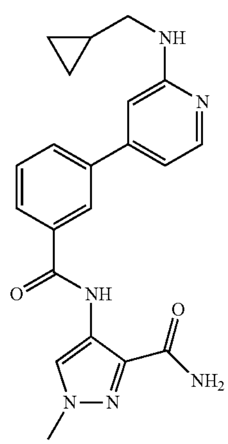 | 184 | 491 [M + H]+, 2.3 min | 400 MHz (DMSO-d6) 10.83 (s, 1H) 8.34 (s, 1H), 8.17 (s, 1H), 7.97-8.03 (M, 2H), 7.82 (s, 1H), 7.76 (t, 1H), 7.56 (s, 1H), 7.32 (s, 1H), 7.20 (d, 1H), 3.92 (s, 3H), 3.25 (s, 2H), 1.13 (m, 1H), 5.55 (m, 2H), 0.30 (m, 2H) |
| 4 | 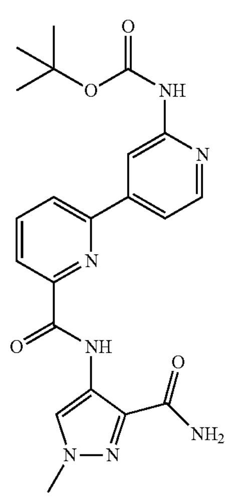 [SMILES: Cn1cc(NC(=O)c2cccc(-c3ccnc(NC(=O)OC(C)(C)C)c3)n2)c(C(N)=O)n1] | 785 | 438 [M + H]+, 1.9 min | 400 MHz (DMSO-d6) 8.44 (d, 1H), 8.42 (s, 1H), 8.38 (d, 1H), 8.23-8.19 (m, 3H), 8.06 (m, 1H). 7.74 (s, 1H), 7.59 (s, 1H), 3.90 (s, 3H), 1.49 (s, 9H) |

| Example | Structure | IRAK4 IC$_{50}$ (nM) | MS m/z & HPLC retention time | NMR |
|---|---|---|---|---|
| 5 | 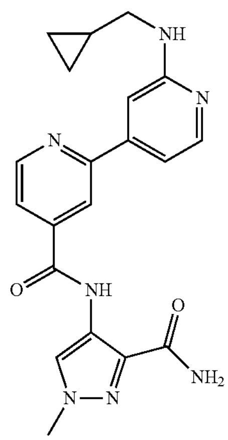 [SMILES: Cn1cc(NC(=O)c2ccnc(-c3ccnc(NCC4CC4)c3)c2)c(C(N)=O)n1] | 1447 | 392 [M + H]+, 1.9 min | 400 MHz (DMSO-d6) 10.94 (s, 1H), 8.89 (d, 1H), 8.36 (s, 1H), 8.19 (s, 1H), 8.09 (d, 1H), 7.85 (s, 1H), 7.75-7.76 (m, 1H), 7.62 (s, 1H), 7.24 (s, 1H), 7.09-7.11 (m, 1H), 6.80 (m, 1H), 3.93 (s, 3H), 3.17 (t, 2H), 1.06 (m, 1H), 0.41-0.44 (m, 2H), 0.19-0.21 (m, 2H) |
| 6 | 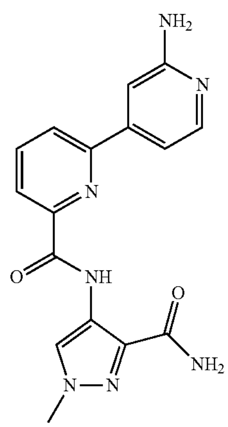 [SMILES: Cn1cc(NC(=O)c2cccc(-c3ccnc(N)c3)n2)c(C(N)=O)n1] | 101 | 338 [M + H]+, 1.5 min | 400 MHz (DMSO-d6) 8.42 (s, 1H), 8.32-8.26 (m, 3H), 8.17 (br s, 1H), 8.11 (m, 1H), 8.09-7.77 (m, 3H), 7.56 (s, 1H), 3.94 (s, 3H) |
| 7 | 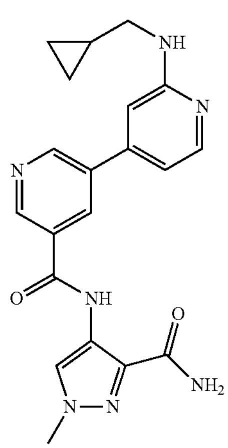 | 1099 | 392 [M + H]+, 1.8 min | 400 MHz (DMSO-d6) 10.85 (s, 1H), 9.13 (d, 2H), 8.49 (s, 1H), 8.34 (s, 1H), 8.04-8.06 (m, 1H), 7.84 (m, 1H), 7.57 (s, 1H), 7.38 (m, 1H), 7.27 (m, 1H), 3.91 (s, 3H), 3.26 (m, 2H), 1.14 (m, 1H), 0.52 (m, 2H), 0.28 (m, 2H) |

-continued

| Example | Structure | IRAK4 IC$_{50}$ (nM) | MS m/z & HPLC retention time | NMR |
|---|---|---|---|---|
| 8 | 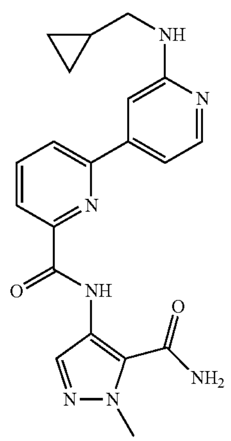 [SMILES: Cn1ncc(NC(=O)c2cccc(-c3ccnc(NCC4CC4)c3)n2)c1C(N)=O] | 2725 | 392 [M + H]+, 1.7 min | 400 MHz (DMSO-d6) 11.19 (s, 1H), 8.13-8.19 (m, 2H), 8.10 (d, 1H), 8.07 (s, 1H), 7.91 (s, 1H), 7.40 (d, 1H), 7.26 (s, 1H), 4.03 (s, 3H), 3.21 (m, 2H), 1.08 (m, 1H), 0.43 (m, 2H), 0.23 (m, 2H) |
| 9 | 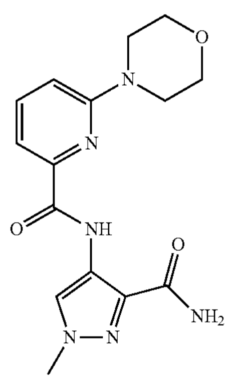 [SMILES: Cn1cc(NC(=O)c2cccc(N3CCOCC3)n2)c(C(N)=O)n1] | 3218 | 331 [M + H]+, 2.0 min | 400 MHz (DMSO-d6) 11.64 (s, 1H), 8.34 (s, 1H), 7.75 (t, 1H), 7.65 (m, 1H), 7.53 (m, 1H), 7.40 (m, 1H), 7.09 (m, 1H), 3.89 (s, 2H), 3.71 (m, 4H), 3.61 (m, 4H) |
| 10 | 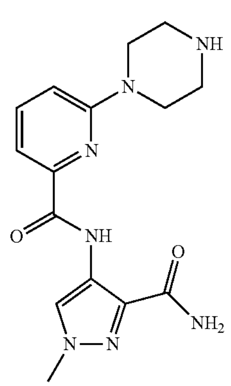 [SMILES: Cn1cc(NC(=O)c2cccc(N3CCNCC3)n2)c(C(N)=O)n1] | 3452 | 330 [M + H]+, 1.3 min | 400 MHz (DMSO-d6) 11.70 (s, 1H), 9.10 (s, 1H), 8.85 (s, 1H), 8.34 (s, 1H), 8.02 (s, 1H), 7.81-7.83 (m, 1H), 7.73 (s, 1H), 7.46 (s, 1H), 7.20 (d, 1H), 3.90 (s, 3H), 3.55 (m, 1H), 3.28 (s, 2H), 3.20 (s, 2H), 3.12 (s, 2H), 3.04 (s, 2H) |

| Example | Structure | IRAK4 IC$_{50}$ (nM) | MS m/z & HPLC retention time | NMR |
|---|---|---|---|---|
| 11 | 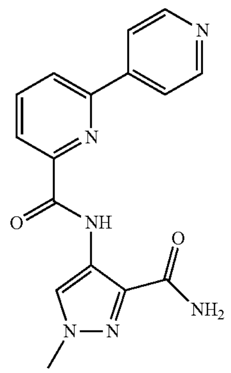 [SMILES: Cn1cc(NC(=O)c2cccc(-c3ccncc3)n2)c(C(N)=O)n1] | 1895 | 323 [M + H]+, 1.4 min | 400 MHz (DMSO-d6) 12.01 (s, 1H), 8.74 (d, 1H), 8.45 (d, 1H), 3.42 (s, 2H), 8.18-8.25 (m, 2H), 7.75 (s, 1H), 7.65 (s, 1H), 3.93 (s, 3H) |
| 12 | 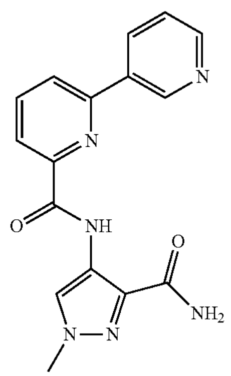 [SMILES: Cn1cc(NC(=O)c2cccc(-c3cccnc3)n2)c(C(N)=O)n1] | 212 | 323 [M + H]+, 1.4 min | 400 MHz (DMSO-d6) 12.03 (s, 1H), 9.55 (s, 1H), 8.70 (d, 2H), 8.38 (m, 2H), 8.13-8.21 (m, 2H), 7.75 (s, 1H), 7.64 (s, 1H), 7.54 (m, 1H), 3.93 (s, 3H) |
| 13 | 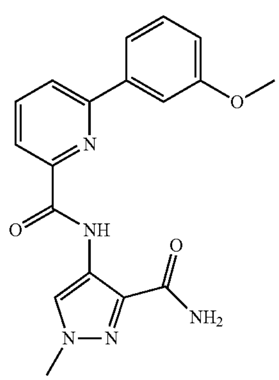 [SMILES: COc1cccc(-c2cccc(C(=O)Nc3cn(C)nc3C(N)=O)n2)c1] | 637 | 352 [M + H]+, 1.0 min | 400 MHz (DMSO-d6) 11.97 (s, 1H), 8.41 (m, 1H), 8.26 (d, 1H), 8.03-8.18 (m, 1H), 7.94 (s, 1H), 7.86 (d, 1H), 7.72 (d, 1H)., 7.50 (s, 1H), 7.41 (t, 1H), 7.04 (d, 1H), 3.93 (s, 6H) |
| 14 | 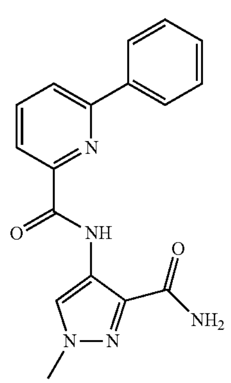 | 3631 | 332 [M + H]+, 2.2 min | 400 MHz (DMSO-d6) 11.96 (s, 1H), 8.06-8.42 (m, 5H), 7.49-7.60 (m, 5H), 3.93 (s, 3H) |

| Example | Structure | IRAK4 IC$_{50}$ (nM) | MS m/z & HPLC retention time | NMR |
|---|---|---|---|---|
| 15 | 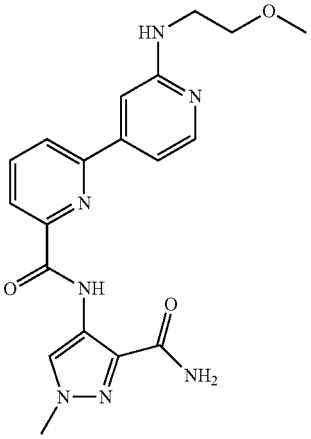 [SMILES: COCCNc1cc(-c2cccc(C(=O)Nc3cn(C)nc3C(N)=O)n2)ccn1] | 187 | 396 [M + H]+, 0.7 min | 400 MHz (CD$_3$OD) 11.83 (s, 1H), 8.19-8.38, (m, 3H), 7.98 (m, 2H), 7.72 (d, 1H), 4.00 (s, 3H), 3.98 (s, 3H), 3.92 (s, 2H), 3.73 (m, 2H) |
| 16 | 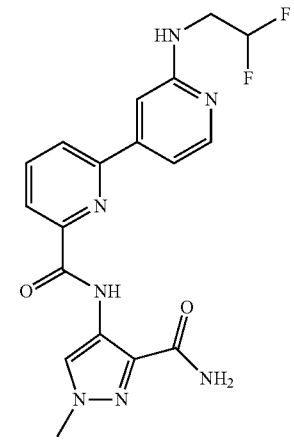 [SMILES: Cn1cc(NC(=O)c2cccc(-c3ccnc(NCC(F)F)c3)n2)c(C(N)=O)n1] | 196 | 402 [M + H]+, 1.7 min | 400 MHz (CD$_3$OD) 11.89 (s, 1H), 8.39 (s, 1H), 8.08-8.15 (m, 3H), 7.68 (m, 1H), 7.61 (m, 1H), 7.44 (d, 1H), 5.88-6.09, (m, 1H), 4.20 (d, 2H), 3.99 (s, 3H) |
| 17 | 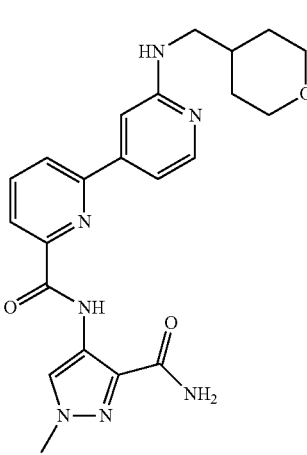 [SMILES: Cn1cc(NC(=O)c2cccc(-c3ccnc(NCC4CCOCC4)c3)n2)c(C(N)=O)n1] | 477 | 436 [M + H]+, 1.7 min | 400 MHz (CD$_3$OD) 11.81 (s, 1H), 8.20-8.40 (m, 3H), 7.90-8.01 (m, 2H), 7.75 (d, 1H), 4.01 (m, 2H), 4.00 (s, 3H), 3.40-3.56 (m, 4H), 2.00-2.10 (m, 1H), 1.81 (m, 2H), 1.40-1.50 (m, 2H) |

| Example | Structure | IRAK4 IC$_{50}$ (nM) | MS m/z & HPLC retention time | NMR |
|---|---|---|---|---|
| 18 | 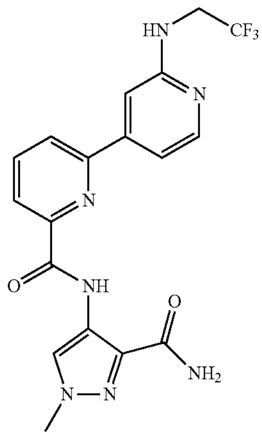 [SMILES: Cn1cc(NC(=O)c2cccc(-c3ccnc(NCC(F)(F)F)c3)n2)c(C(N)=O)n1] | 127 | 420 [M + H]+, 1.8 min | 400 MHz (CD$_3$OD) 11.89 (s, 1H), 8.39 (s, 1H), 8.08-8.23 (m, 3H), 7.61 (s, 1H), 7.48 (d, 1H), 3.99 (s, 3H), 3.34 (m, 2H) |
| 19 | 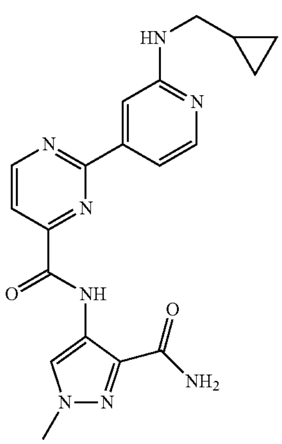 [SMILES: Cn1cc(NC(=O)c2ccnc(-c3ccnc(NCC4CC4)c3)n2)c(C(N)=O)n1] | 283 | 393 [M + H]+, 1.8 min | 400 MHz (CD$_3$OD) 11.82 (s, 1H), 9.23 (d, 1H), 8.4 (s, 1H), 8.21 (m, 2H), 7.98 (q, 3H), 4.00 (s, 3H), 3.36 (m, 2H), 1.22 (m, 1H), 0.73 (q, 2H), 0.41 (m, 2H) |

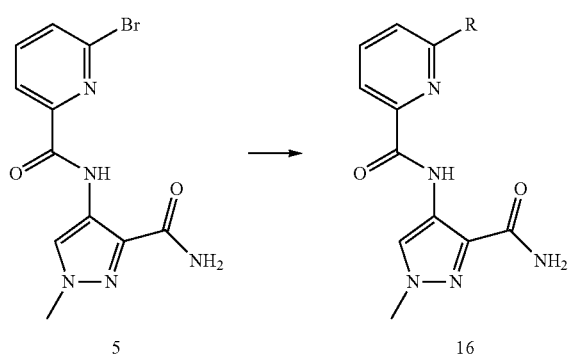

General Procedure: 6-Bromo-N-(3-carbamoyl-1-methyl-1H-pyrazol-4-yl)picolinamide, (1 equiv), boronic acid (1.1 equiv) and Pd(dppf)Cl$_2$ are combined in a flask and K$_2$CO$_3$ (2 equiv, 1M in water) and THF (0.05 M) are added. The mixture is degassed and heated to reflux for 6 h. The reaction mixture is cooled to room temperature and purified by reverse phase HPLC.

Analytical HPLC conditions: The mobile phase (H$_2$O/acetonitrile) contains 0.1% NH$_3$ and the gradients run from 5% to 100% acetonitrile, hold for 0.4 min, then go back to initial condition of 5% acetonitrile. Total run time is 2 min for each sample.

| Time (min) | Flow (ml/min) | H$_2$O % | Acetonitrile % |
|---|---|---|---|
| 0 | 1 | 95 | 5 |
| 1.4 | 1 | 0 | 100 |
| 1.8 | 1 | 0 | 100 |
| 2.0 | 1 | 95 | 5 |

The following compounds were thus obtained:

| Example | Structure | IRAK4 IC$_{50}$ (nM) | MS m/z & HPLC retention time |
|---|---|---|---|
| 20 | 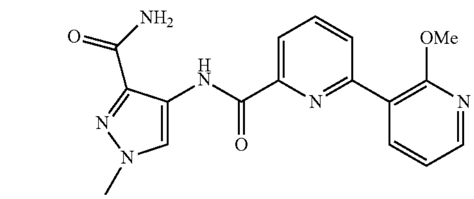 [SMILES: COc1ncccc1-c1cccc(C(=O)Nc2cn(C)nc2C(N)=O)n1] | 2134 | 352 [M + H]+, 0.82 min |
| 21 | 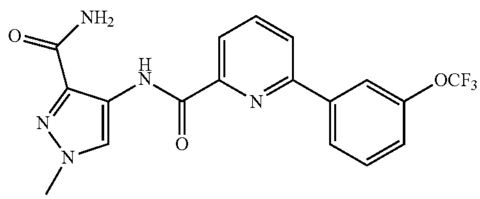 [SMILES: Cn1cc(NC(=O)c2cccc(-c3cccc(OC(F)(F)F)c3)n2)c(C(N)=O)n1] | 2257 | 405 [M + H]+, 1.01 min |
| 22 | 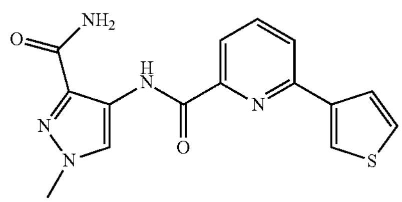 [SMILES: Cn1cc(NC(=O)c2cccc(-c3ccsc3)n2)c(C(N)=O)n1] | 362 | 327 [M + H]+, 0.82 min |
| 23 | 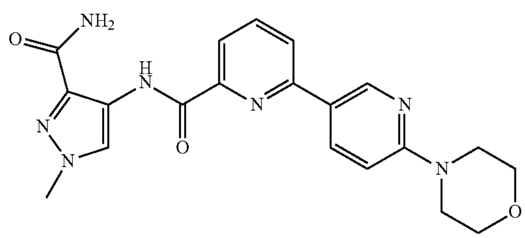 [SMILES: Cn1cc(NC(=O)c2cccc(-c3ccc(N4CCOCC4)nc3)n2)c(C(N)=O)n1] | 1105 | 407 [M + H]+, 0.79 min |
| 24 | 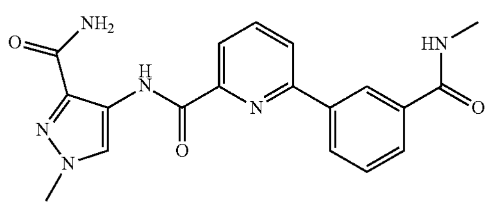 [SMILES: CNC(=O)c1cccc(-c2cccc(C(=O)Nc3cn(C)nc3C(N)=O)n2)c1] | 201 | 378 [M + H]+, 0.74 min |
| 25 | 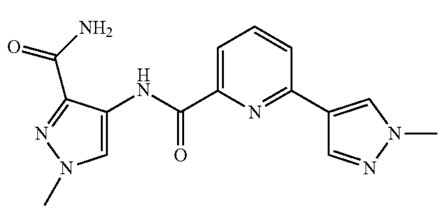 [SMILES: Cn1cc(-c2cccc(C(=O)Nc3cn(C)nc3C(N)=O)n2)cn1] | 32 | 325 [M + H]+, 0.66 min |
| 26 | 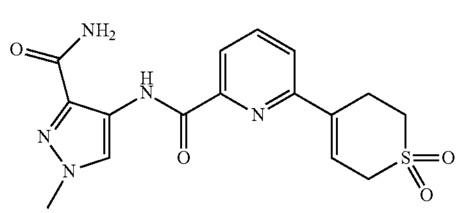 [SMILES: Cn1cc(NC(=O)c2cccc(C3=CCS(=O)(=O)CC3)n2)c(C(N)=O)n1] | 1299 | 375 [M + H]+, 0.62 min |

-continued
| Example | Structure | IRAK4 IC$_{50}$ (nM) | MS m/z & HPLC retention time |
|---|---|---|---|
| 27 | 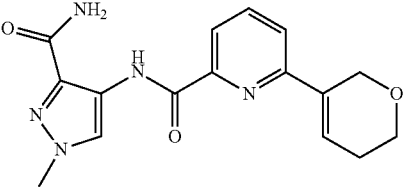 [SMILES: Cn1cc(NC(=O)c2cccc(C3=CCCOC3)n2)c(C(N)=O)n1] | 134 | 327 [M + H]+, 0.74 min |
| 28 | 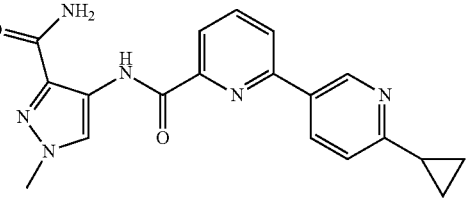 | 94 | 362 [M + H]+, 0.85 min |
| 29 | 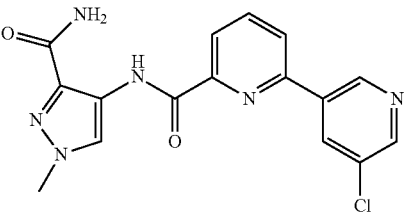 [SMILES: Cn1cc(NC(=O)c2cccc(-c3cncc(Cl)c3)n2)c(C(N)=O)n1] | 91 | 356 [M + H]+, 0.79 min |
| 30 | 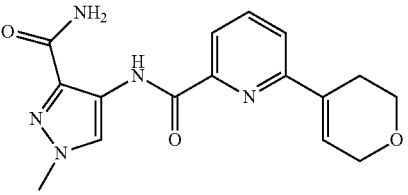 [SMILES: Cn1cc(NC(=O)c2cccc(C3=CCOCC3)n2)c(C(N)=O)n1] | 426 | 327 [M + H]+, 0.71 min |
| 31 | 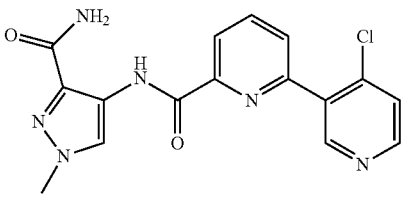 [SMILES: Cn1cc(NC(=O)c2cccc(-c3cnccc3Cl)n2)c(C(N)=O)n1] | 620 | 356 [M + H]+, 0.75 min |
| 32 | 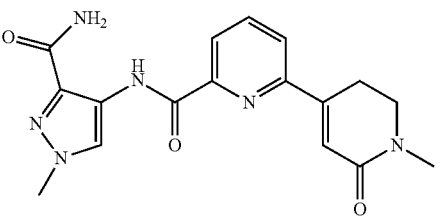 [SMILES: CN1CCC(c2cccc(C(=O)Nc3cn(C)nc3C(N)=O)n2)=CC1=O] | 82 | 354 [M + H]+, 0.63 min |
| 33 | 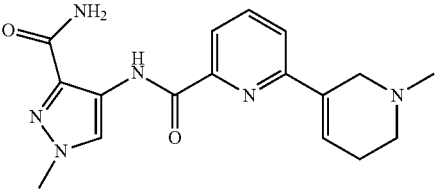 [SMILES: CN1CCC=C(c2cccc(C(=O)Nc3cn(C)nc3C(N)=O)n2)C1] | 739 | 341 [M + H]+, 0.69 min |

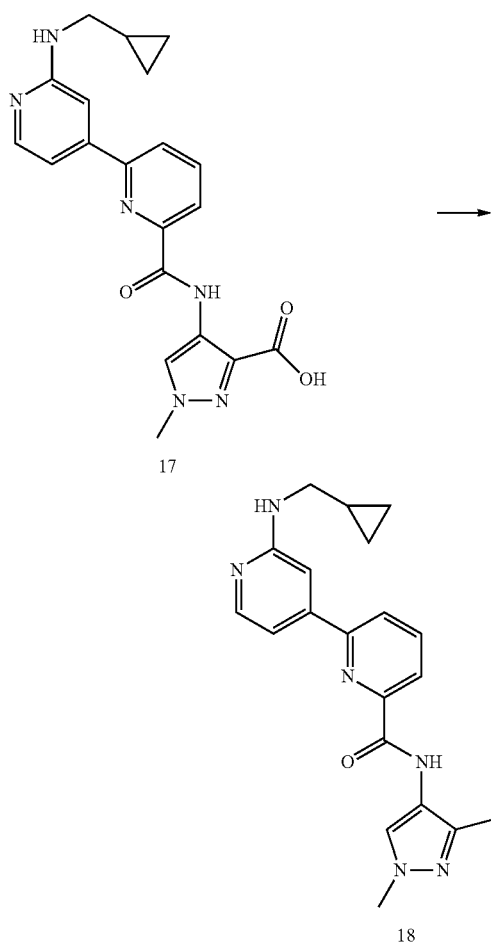

Procedure for Synthesis of Amides:

Step 1: A 1 dram vial was charged with 4-(2'-((tert-butoxycarbonyl)(cyclopropylmethyl)amino)-[2,4'-bipyridine]-6-carboxamido)-1-methyl-1H-pyrazole-3-carboxylic acid (10 mg, 0.020 mmol), the amine (1.3 eq., 0.026 mmol), TBTU (1.5 eq., 9.78 mg, 0.030 mmol) and a solution of $CH_2Cl_2$ (125 DMF (10 μL) and DIPEA (3 eq., 10.6 μL, 0.061 mmol). The reaction mixtures were shaken overnight. The reaction was checked with LC/MS. In most reactions, the major peak was the desired product. However, in the case of pyrimidin-5-amine, the reaction was not complete, so 5 mg of NaH was added to the reaction mixture, then it was shaken for 2 more hours, and the reaction was complete. The reaction mixtures were carried to the next step without further purification.

Step 2: To the above reaction mixture, was added a solution of $CH_2Cl_2$ (200 μL) and TFA (200 μL, 2.60 mmol). The mixture was shaken for 3 h. LC/MS demonstrated the reaction was complete. Volatiles were removed with a GeneVac. 0.45 mL DMSO was added to dissolve the mixture. The mixture was filtered and then purified using mass directed reverse phase HPLC.

| Example | Structure | IRAK4 $IC_{50}$ (nM) | MS m/z & HPLC retention time |
|---|---|---|---|
| 34 | 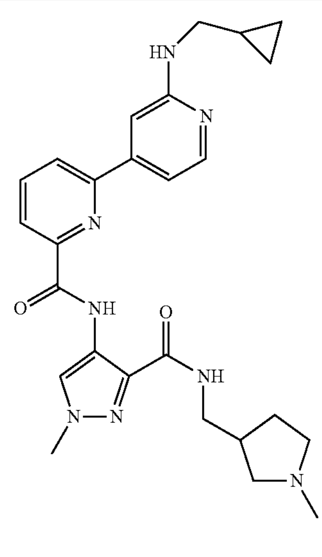 [SMILES: CN1CCC(CNC(=O)c2nn(C)cc2NC(=O)c2cccc(-c3ccnc(NCC4CC4)c3)n2)C1] | 729 | 489 [M + H]+, 1.07 min |

-continued

| Example | Structure | IRAK4 IC$_{50}$ (nM) | MS m/z & HPLC retention time |
|---|---|---|---|
| 35 | 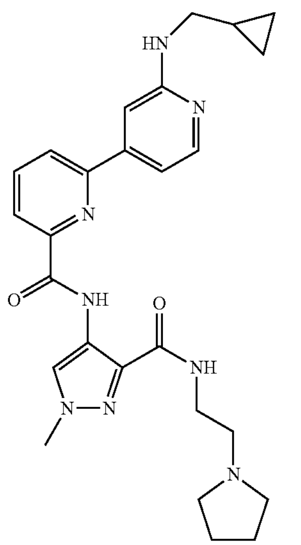 [SMILES: Cn1cc(NC(=O)c2cccc(-c3ccnc(NCC4CC4)c3)n2)c(C(=O)NCCN2CCCC2)n1] | 1062 | 489 [M + H]+, 1.10 min |
| 36 | 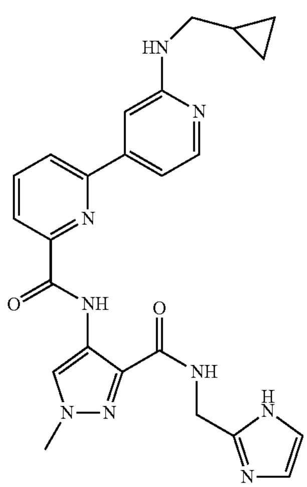 [SMILES: Cn1cc(NC(=O)c2cccc(-c3ccnc(NCC4CC4)c3)n2)c(C(=O)NCc2ncc[nH]2)n1] | 1543 | 472 [M + H]+, 0.85 min |
| 37 | 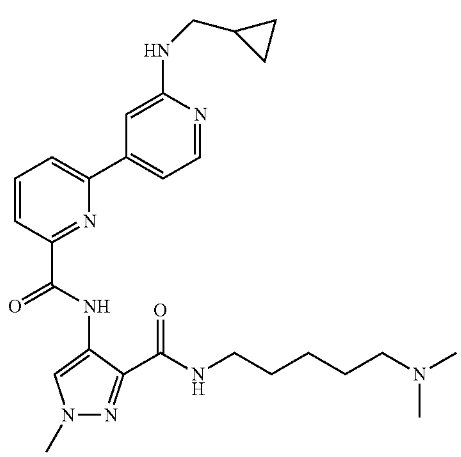 [SMILES: CN(C)CCCCCNC(=O)c1nn(C)cc1NC(=O)c1cccc(-c2ccnc(NCC3CC3)c2)n1] | 2187 | 505 [M + H]+, 1.20 min ) |

-continued
| Example | Structure | IRAK4 IC$_{50}$ (nM) | MS m/z & HPLC retention time |
|---|---|---|---|
| 38 | 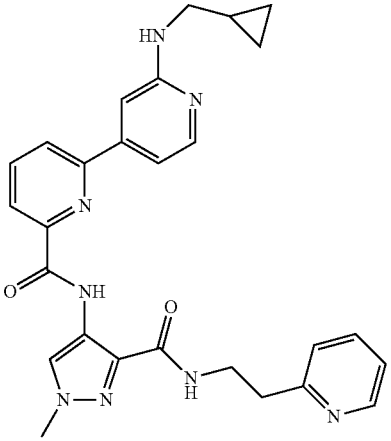 [SMILES: Cn1cc(NC(=O)c2cccc(-c3ccnc(NCC4CC4)c3)n2)c(C(=O)NCCc2ccccn2)n1] | 4971 | 497 [M + H]+, 1.01 min |
| 39 | 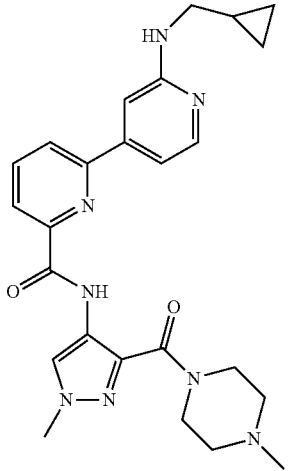 [SMILES: CN1CCN(C(=O)c2nn(C)cc2NC(=O)c2cccc(-c3ccnc(NCC4CC4)c3)n2)CC1] | 2914 | 475 [M + H]+, 0.98 min |
| 40 | 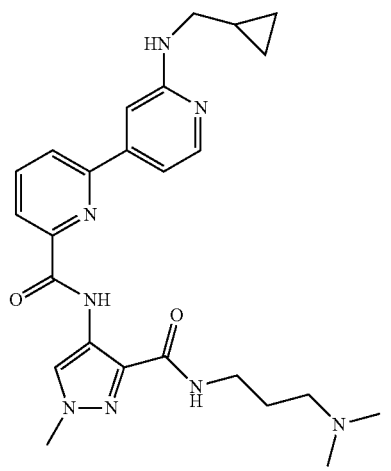 [SMILES: CN(C)CCCNC(=O)c1nn(C)cc1NC(=O)c1cccc(-c2ccnc(NCC3CC3)c2)n1] | 535 | 477 [M + H]+, 1.05 min |

-continued
| Example | Structure | IRAK4 IC$_{50}$ (nM) | MS m/z & HPLC retention time |
|---|---|---|---|
| 41 | 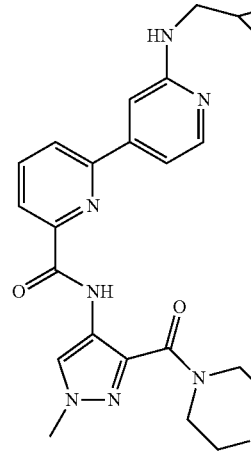 | 1829 | 476 [M + H]+, 0.99 min |
| 42 | 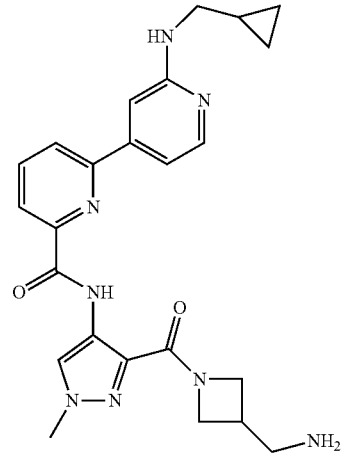 [SMILES: Cn1cc(NC(=O)c2cccc(-c3ccnc(NCC4CC4)c3)n2)c(C(=O)N2CC(CN)C2)n1] | 190 | 461 [M + H]+, 0.90 min |
| 43 | 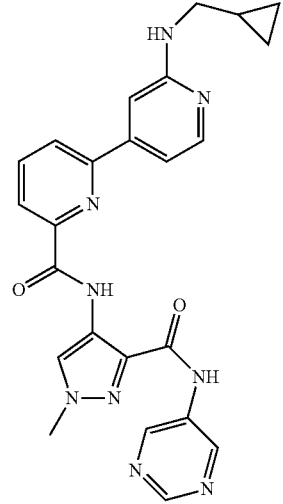 [SMILES: Cn1cc(NC(=O)c2cccc(-c3ccnc(NCC4CC4)c3)n2)c(C(=O)Nc2cncnc2)n1] | 1581 | 470 [M + H]+, 0.93 min |

-continued
| Example | Structure | IRAK4 IC$_{50}$ (nM) | MS m/z & HPLC retention time |
|---|---|---|---|
| 44 | 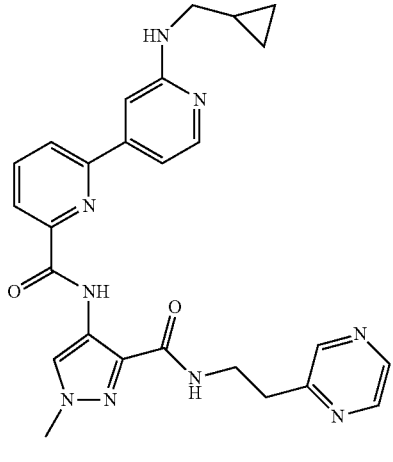 [SMILES: Cn1cc(NC(=O)c2cccc(-c3ccnc(NCC4CC4)c3)n2)c(C(=O)NCCc2cnccn2)n1] | 2673 | 498 [M + H]+, 0.95 min |
| 45 | 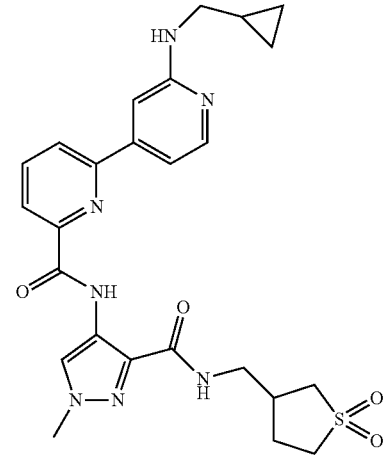 [SMILES: Cn1cc(NC(=O)c2cccc(-c3ccnc(NCC4CC4)c3)n2)c(C(=O)NCC2CCS(=O)(=O)C2)n1] | 3616 | 524 [M + H]+, 0.90 min |
| 46 | 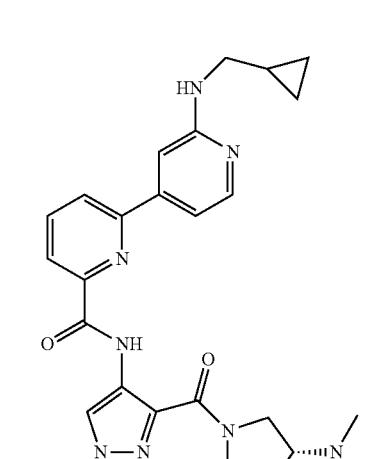 | 186 | 505 [M + H]+, 0.88 min |

| Example | Structure | IRAK4 IC$_{50}$ (nM) | MS m/z & HPLC retention time |
|---|---|---|---|
| 47 | 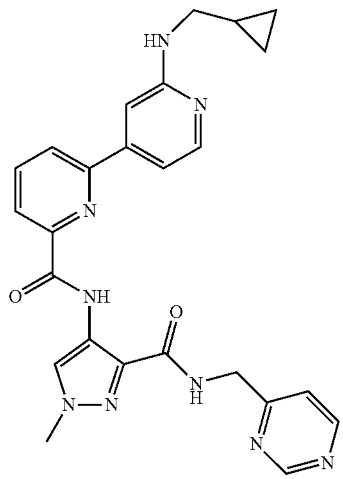 [SMILES: Cn1cc(NC(=O)c2cccc(-c3ccnc(NCC4CC4)c3)n2)c(C(=O)NCc2ccncn2)n1] | 4381 | 484 [M + H]+, 0.90 min |
| 48 | 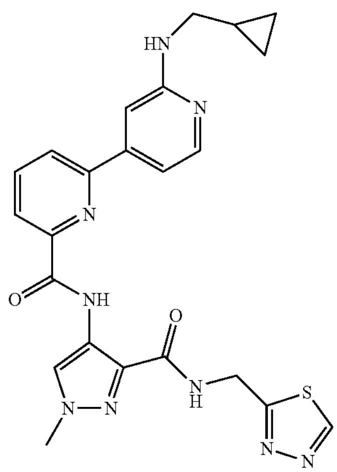 [SMILES: Cn1cc(NC(=O)c2cccc(-c3ccnc(NCC4CC4)c3)n2)c(C(=O)NCc2nncs2)n1] | 2428 | 490 [M + H]+, 0.89 min |
| 49 | 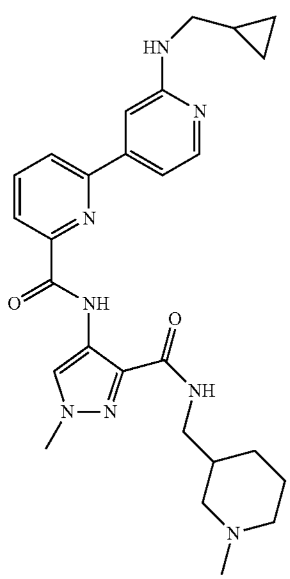 [SMILES: CN1CCCC(CNC(=O)c2nn(C)cc2NC(=O)c2cccc(-c3ccnc(NCC4CC4)c3)n2)C1] | 260 | 503 [M + H]+, 1.07 min |

-continued

| Example | Structure | IRAK4 IC$_{50}$ (nM) | MS m/z & HPLC retention time |
|---|---|---|---|
| 50 | 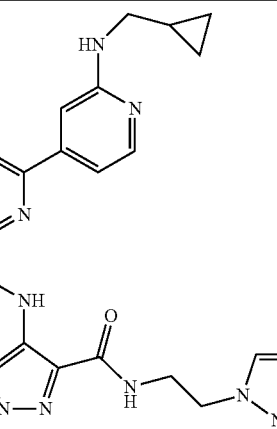 | 2677 | 486 [M + H]+, 0.97 min |
| 51 | 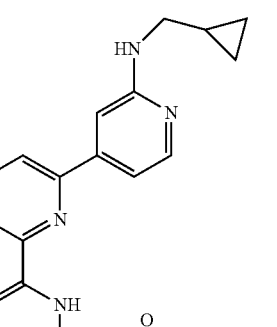 | 2285 | 462 [M + H]+, 0.96 min |

What is claimed is:

1. A compound of Formula III:

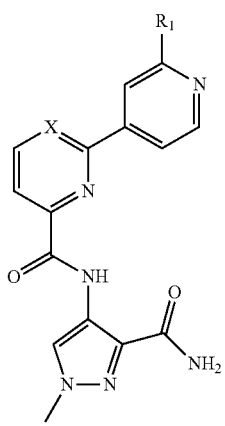

wherein:
X is CH;
a is 0 or 1; b is 0 or 1 m is 0, 1 or 2;

$R_1$ is selected from: H, oxo, (C=O)$_a$O$_b$(C$_1$-C$_{10}$) alkyl, (C=O)$_a$O$_b$-aryl, (C=O)$_a$O$_b$(C$_2$-C$_{10}$)alkenyl, (C=O)$_a$O$_b$(C$_2$-C$_{10}$)alkynyl, CO$_2$H, halo, OH, O$_b$(C$_1$-C$_6$)perfluoroalkyl, (C=O)$_a$NR$_5$R$_6$, CN, (C=O)$_a$O$_b$(C$_3$-C$_8$)cycloalkyl, S(O)$_m$NR$_5$R$_6$, SH, and S(O)$_m$-(C$_1$-C$_{10}$)alkyl, said alkyl, aryl, alkenyl, alkynyl, and cycloalkyl are optionally substituted with one or more substituents selected from R$_a$;

$R_5$ and $R_6$ are independently selected from: H, (C=O)$_a$O$_b$(C$_a$-C$_{10}$)alkyl, (C=O)$_a$O$_b$-aryl, (C=O)$_a$O$_b$(C$_2$-C$_{10}$)alkenyl, (C=O)$_a$O$_b$(C$_2$-C$_{10}$)alkynyl, CO$_2$H, O$_b$(C$_1$-C$_6$)perfluoroalkyl, (C=O)$_a$N(R$_a$)$_2$, CN, (C=O)$_a$O$_b$(C$_3$-C$_8$)cycloalkyl, S(O)$_m$N(R$_a$)$_2$, SH, and S(O)$_m$-(C$_1$-C$_{10}$)alkyl, said alkyl, aryl, alkenyl, alkynyl, and cycloalkyl are optionally substituted with one or more substituents selected from R$_a$;

$R_a$ is independently selected from R$_b$, OH, (C$_1$-C$_6$)alkoxy, halogen, cyclopropyl, CO$_2$H, CN, O$_a$(C=O)$_b$(C$_1$-C$_6$) alkyl, oxo, and N(R$_b$)$_2$; and $R_b$ is independently selected from H and (C$_1$-C$_6$)alkyl;

or a pharmaceutically acceptable salt or a stereoisomer thereof.

2. A compound which is selected from:
N-(3-carbamoyl-1-methyl-1H-pyrazol-4-yl)-2'-((cyclopropylmethyl)amino)-[2,4'-bipyridine]-6-carboxamide;

tert-butyl(6-((3-carbamoyl-1-methyl-1H-pyrazol-4-yl)carbamoyl)[2,4'-bipyridin]-2'-yl)carbamate;

2'-amino-N-(3-carbamoyl-1-methyl-1H-pyrazol-4-yl)[2,4'-bipyridine]-6-carboxamide;

N-(3-carbamoyl-1-methyl-1H-pyrazol-4-yl)-2,4'-bipyridine-6-carboxamide;

N-(3-carbamoyl-1-methyl-1H-pyrazol-4-yl)-2'-((2-methoxyethyl)amino)-[2,4'-bipyridine]-6-carboxamide;

N-(3-carbamoyl-1-methyl-1H-pyrazol-4-yl)-2'-((2,2-difluoroethyl)amino)-[2,4'-bipyridine]-6-carboxamide; and N-(3-carbamoyl-1-methyl-1H-pyrazol-4-yl)-2'-((2,2,2-trifluoroethyl)amino)-[2,4'-bipyridine]-6-carboxamide;

or a pharmaceutically acceptable salt or stereoisomer thereof.

3. A pharmaceutical composition comprising a pharmaceutical carrier, and dispersed therein, a therapeutically effective amount of a compound of claim 1.

* * * * *